United States Patent
Shrivastava

(10) Patent No.: US 9,060,849 B2
(45) Date of Patent: Jun. 23, 2015

(54) IMPLANTABLE LUMEN FILTER WITH ENHANCED DURABILITY

(75) Inventor: Sanjay Shrivastava, Irvine, CA (US)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 469 days.

(21) Appl. No.: 13/131,255

(22) PCT Filed: Dec. 16, 2009

(86) PCT No.: PCT/US2009/068287
§ 371 (c)(1),
(2), (4) Date: Dec. 12, 2011

(87) PCT Pub. No.: WO2010/077963
PCT Pub. Date: Jul. 8, 2010

(65) Prior Publication Data
US 2012/0071914 A1 Mar. 22, 2012

Related U.S. Application Data

(60) Provisional application No. 61/138,470, filed on Dec. 17, 2008.

(51) Int. Cl.
*A61M 29/00* (2006.01)
*A61F 2/01* (2006.01)

(52) U.S. Cl.
CPC .............. *A61F 2/01* (2013.01); *A61F 2002/011* (2013.01); *A61F 2250/0067* (2013.01); *A61F 2002/016* (2013.01); *A61F 2230/005* (2013.01); *A61F 2230/0067* (2013.01)

(58) Field of Classification Search
CPC ............... A61F 2/00; A61F 2/18; A61F 2/20; A61F 2/06; A61F 2002/30214; A61F 2/01

USPC ......... 606/200, 127, 159, 158, 113, 114, 110; 604/104–107
See application file for complete search history.

(56) References Cited

U.S. PATENT DOCUMENTS 6,142,987 A * 11/2000 Tsugita .......................... 604/500
6,171,328 B1 * 1/2001 Addis ............................ 606/200
(Continued)

FOREIGN PATENT DOCUMENTS

EP 0462008 12/1991
EP 1138277 10/2001
(Continued)

OTHER PUBLICATIONS

U.S. Appl. No. 13/140,369, filed Jun. 16, 2011, Shirvastava et al.
(Continued)

*Primary Examiner* — Katrina Stransky
(74) *Attorney, Agent, or Firm* — Workman Nydegger; Jonathan D. Feuchtwang

(57) ABSTRACT

An implantable lumen filter (100) is described. The implantable lumen filter includes a proximal portion (103*a*) having a generally-tapered outer surface defined by a plurality of outer struts (106). The implantable lumen filter may also include a distal portion (103*b*) having a generally-tapered outer surface defined by a plurality of outer struts (106*b*) coupled together at the distal end (102*b*) of the distal portion. The implantable lumen filter may also include an apex (105) comprising the connection between the proximal and distal portions. The apex may define an outer dimension of the implantable lumen filter. The outer surface of the proximal portion is dimensioned to direct particulates towards the outer dimension.

14 Claims, 16 Drawing Sheets

(56) References Cited

U.S. PATENT DOCUMENTS

| | | | |
|---|---|---|---|
| 6,214,025 B1 | 4/2001 | Thistle et al. | |
| 6,245,012 B1* | 6/2001 | Kleshinski | 623/1.11 |
| 6,267,777 B1* | 7/2001 | Bosma et al. | 606/200 |
| 6,443,972 B1 | 9/2002 | Bosma et al. | |
| 6,468,291 B2* | 10/2002 | Bates et al. | 606/200 |
| 6,517,559 B1* | 2/2003 | O'Connell | 606/158 |
| 6,540,722 B1* | 4/2003 | Boyle et al. | 604/106 |
| 6,702,834 B1* | 3/2004 | Boylan et al. | 606/200 |
| 2001/0025187 A1* | 9/2001 | Okada | 606/200 |
| 2003/0149475 A1 | 8/2003 | Hyodoh et al. | |
| 2003/0208224 A1* | 11/2003 | Broome | 606/200 |
| 2003/0208227 A1* | 11/2003 | Thomas | 606/200 |
| 2005/0004596 A1 | 1/2005 | McGuckin, Jr. et al. | |
| 2005/0131452 A1 | 6/2005 | Walak et al. | |
| 2006/0025852 A1 | 2/2006 | Armstrong et al. | |
| 2006/0058836 A1* | 3/2006 | Bose et al. | 606/200 |
| 2008/0097518 A1 | 4/2008 | Thinnes, Jr. et al. | |

FOREIGN PATENT DOCUMENTS

| | | |
|---|---|---|
| EP | 1557137 | 7/2005 |
| WO | WO00/56390 | 9/2000 |
| WO | WO2007/067451 | 6/2007 |
| WO | WO2008/066881 | 6/2008 |
| WO | WO2010/077963 | 7/2010 |
| WO | WO2010/077973 | 7/2010 |

OTHER PUBLICATIONS

U.S. Appl. No. 61/138,458, filed Dec. 17, 2008, Shrivastava et al.
U.S. Appl. No. 61/138,466, filed Dec. 17, 2008, Shrivastava et al.
U.S. Appl. No. 61/138,470, filed Dec. 17, 2008, Shrivastava.
U.S. Appl. No. 61/138,485, filed Dec. 17, 2008, Obradovic.
U.S. Appl. No. 61/138,509, filed Dec. 17, 2008, Shrivastava et al.

* cited by examiner

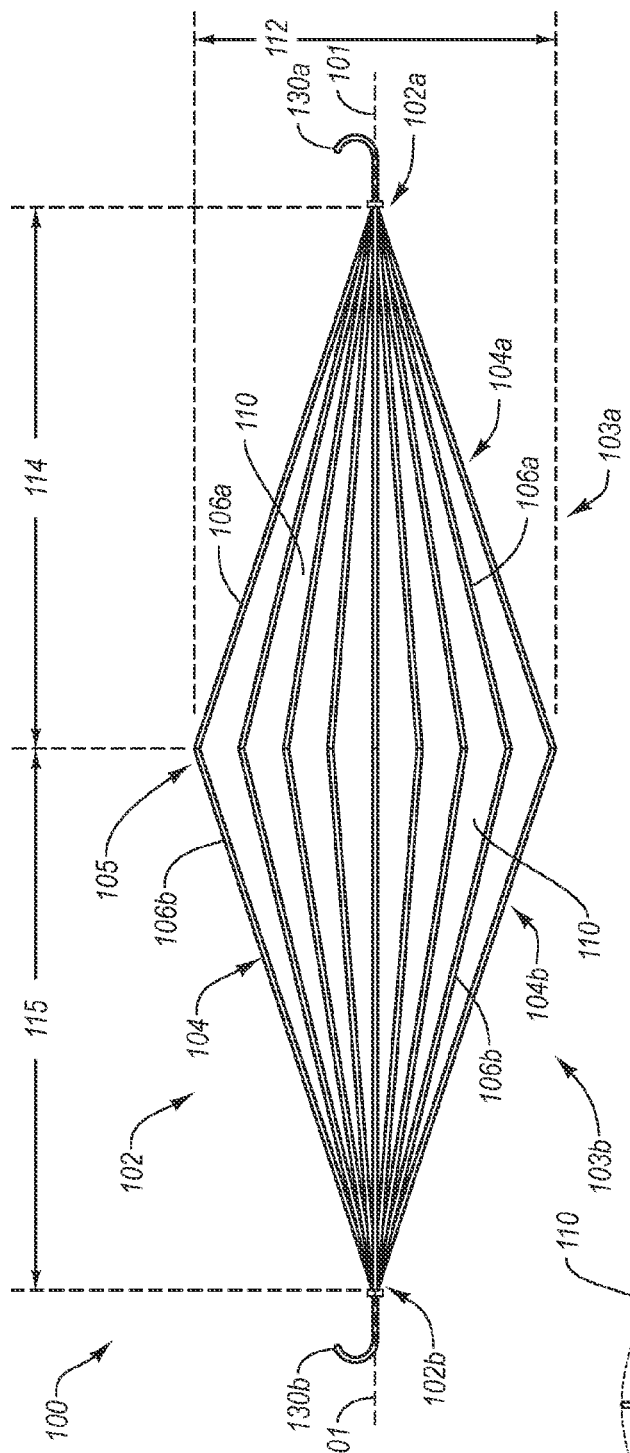
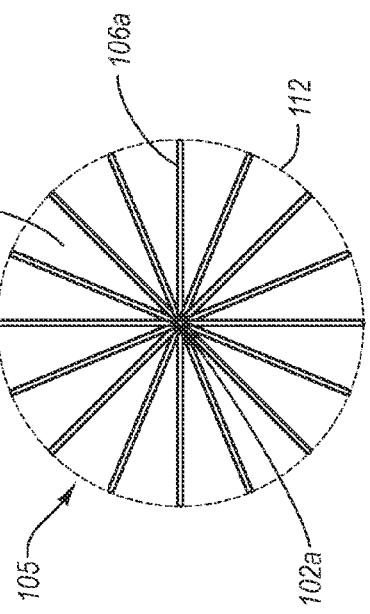
Fig. 1A
Fig. 1B

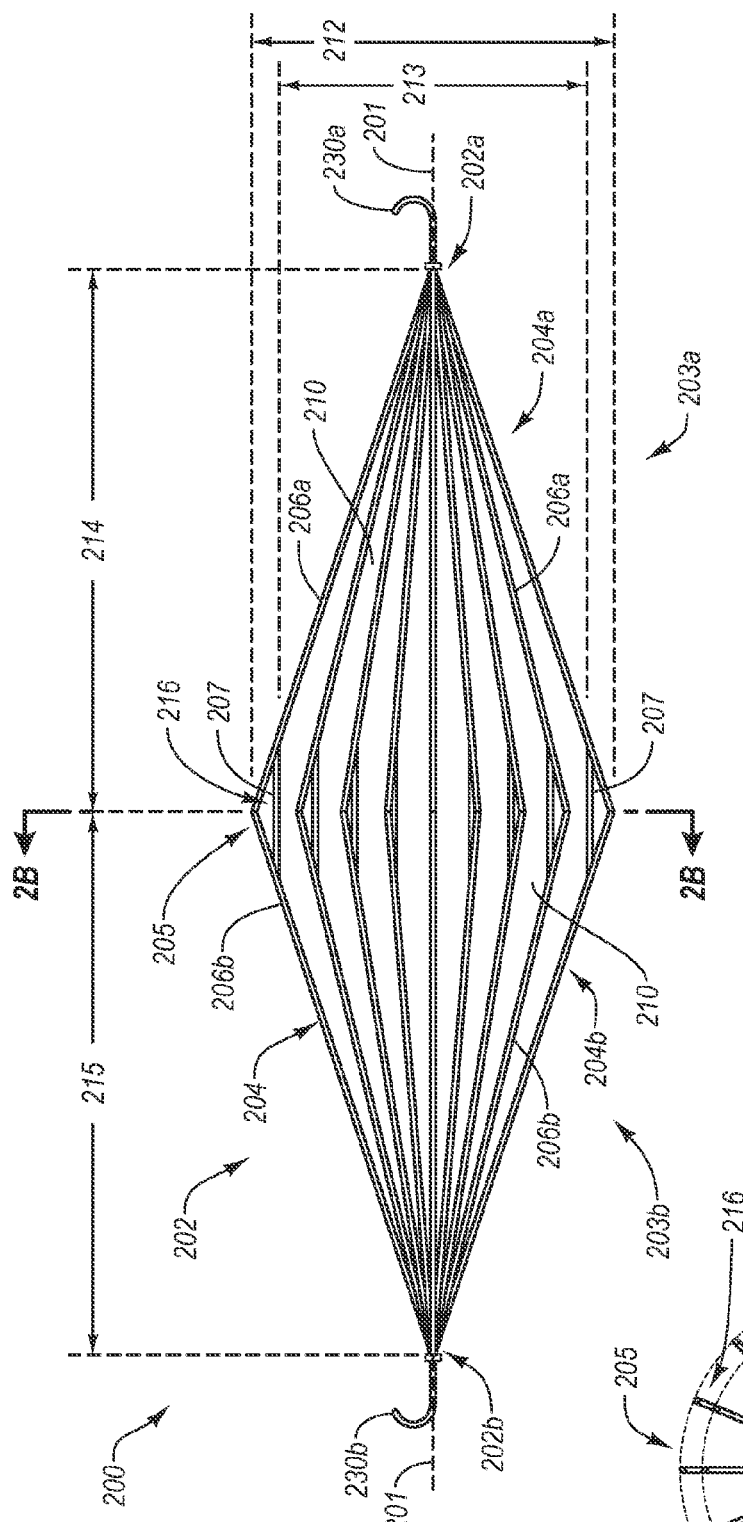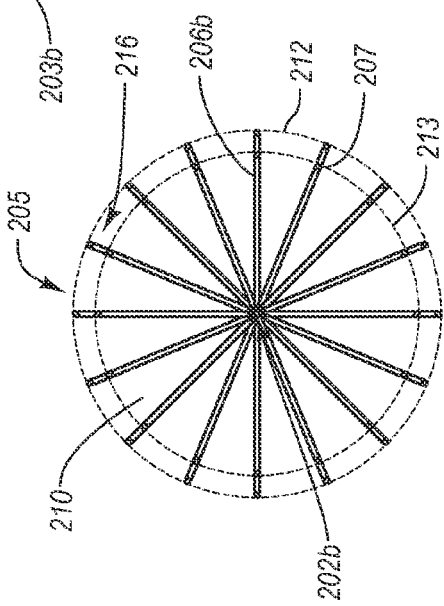
Fig. 2A
Fig. 2B

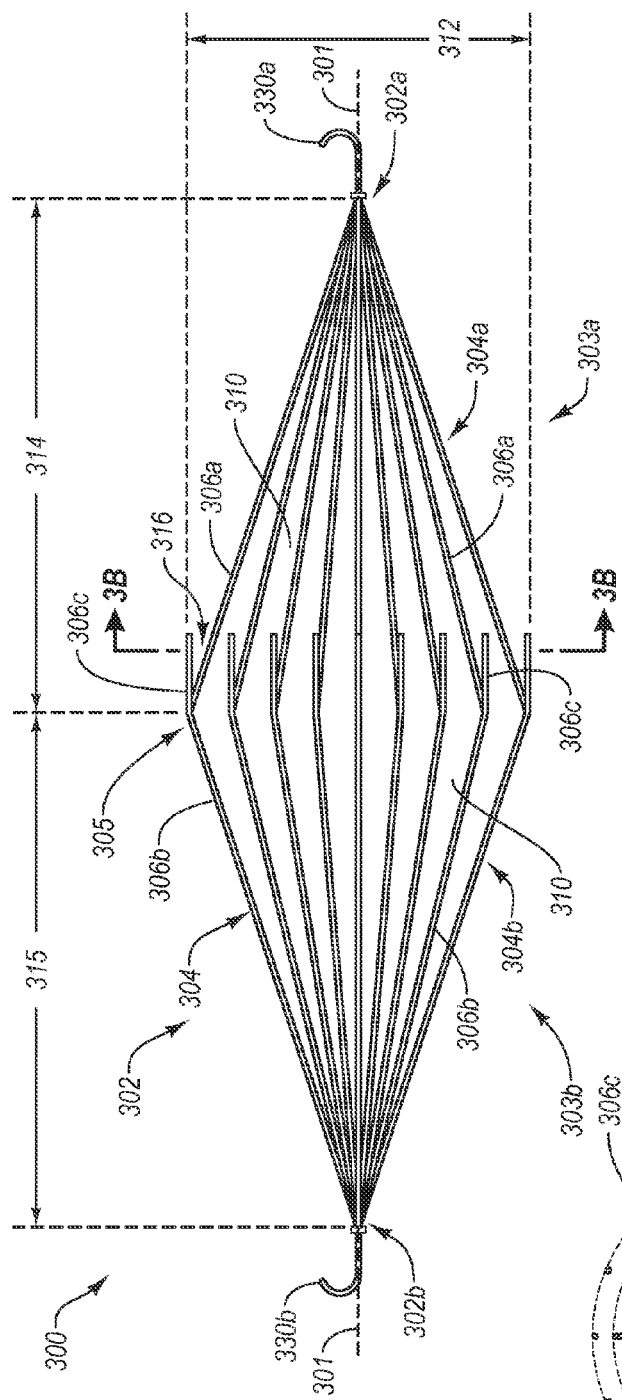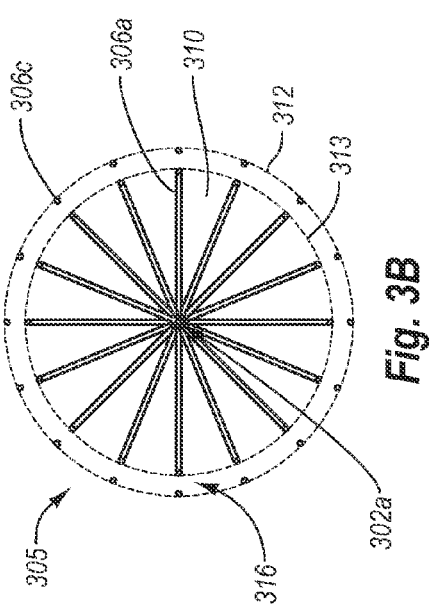
Fig. 3A
Fig. 3B

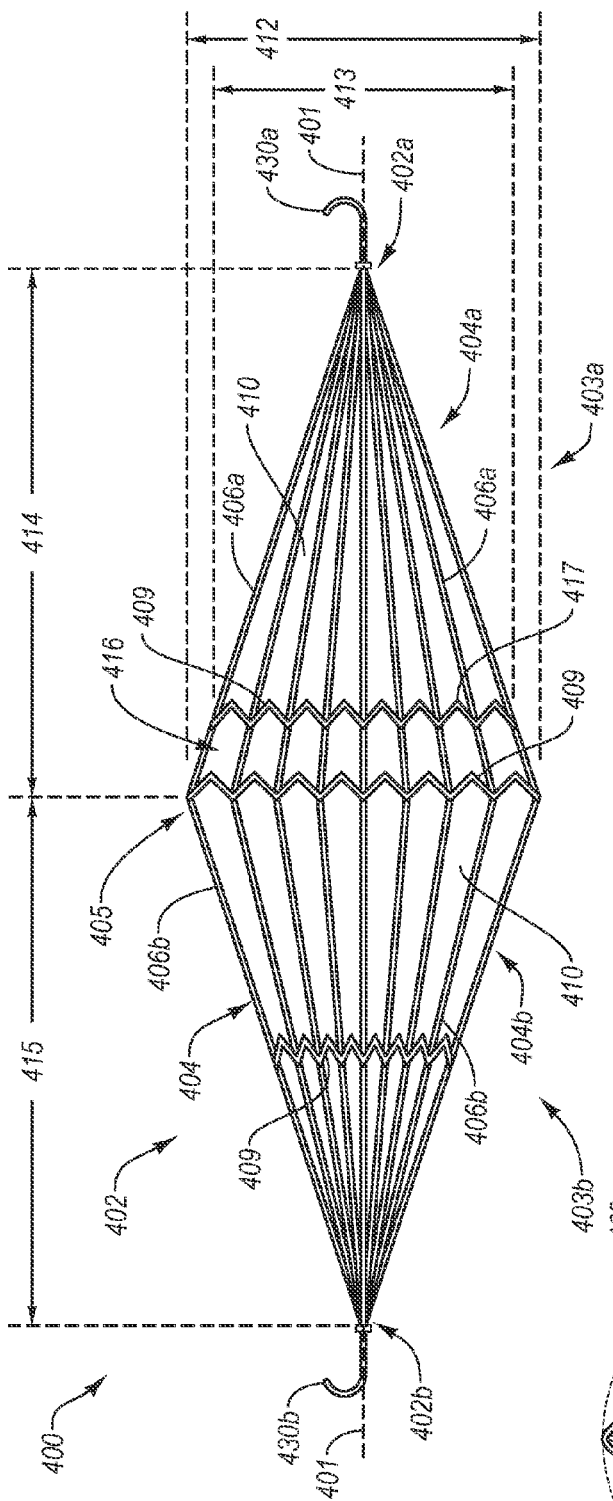
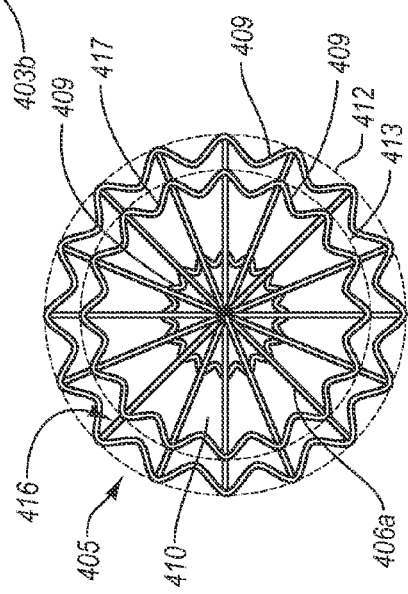
Fig. 4A
Fig. 4B

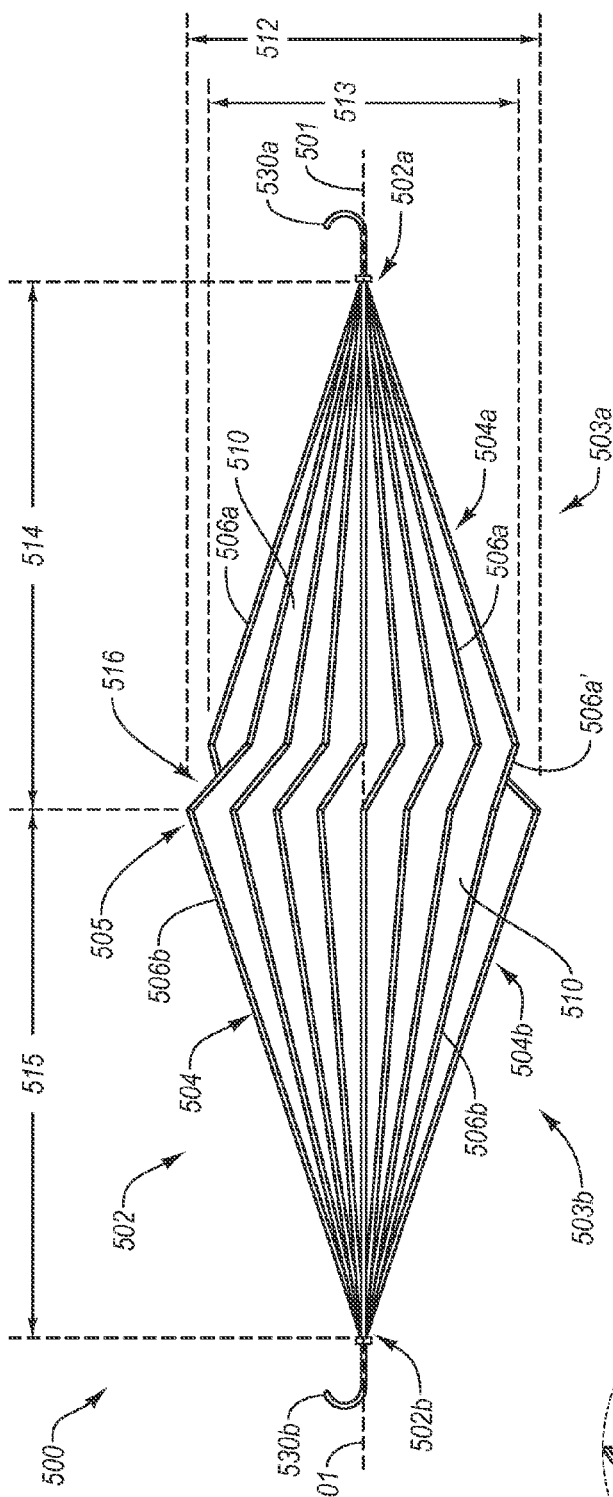
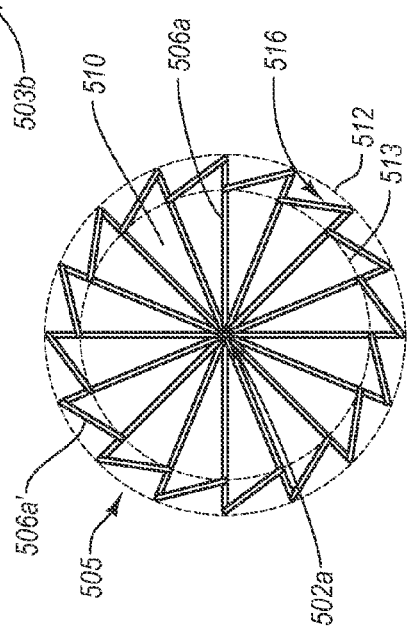

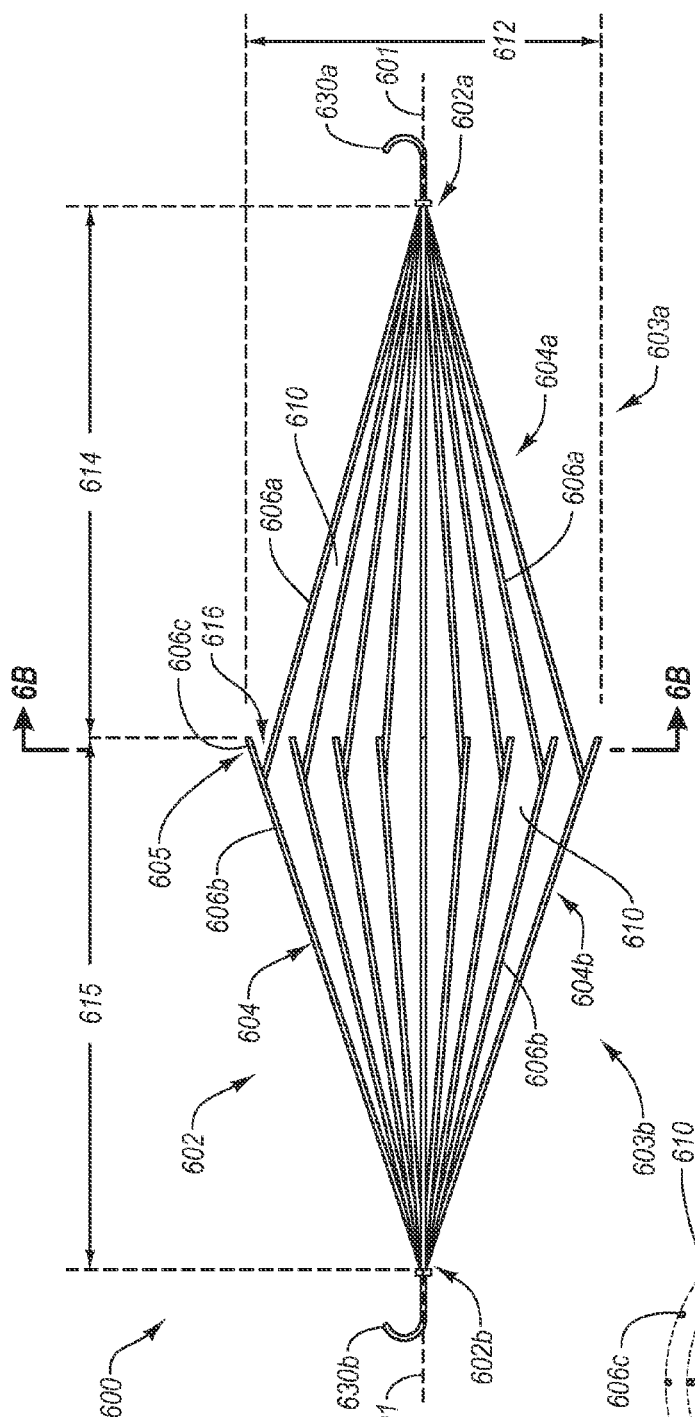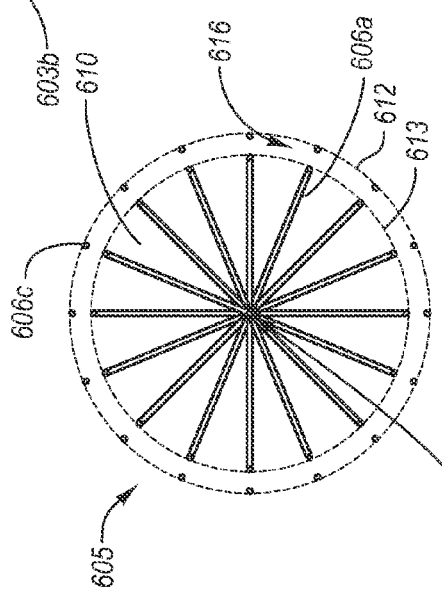

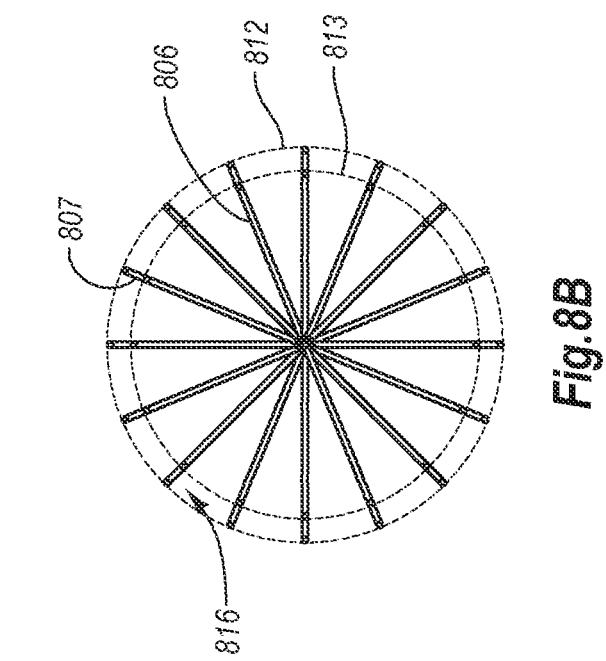
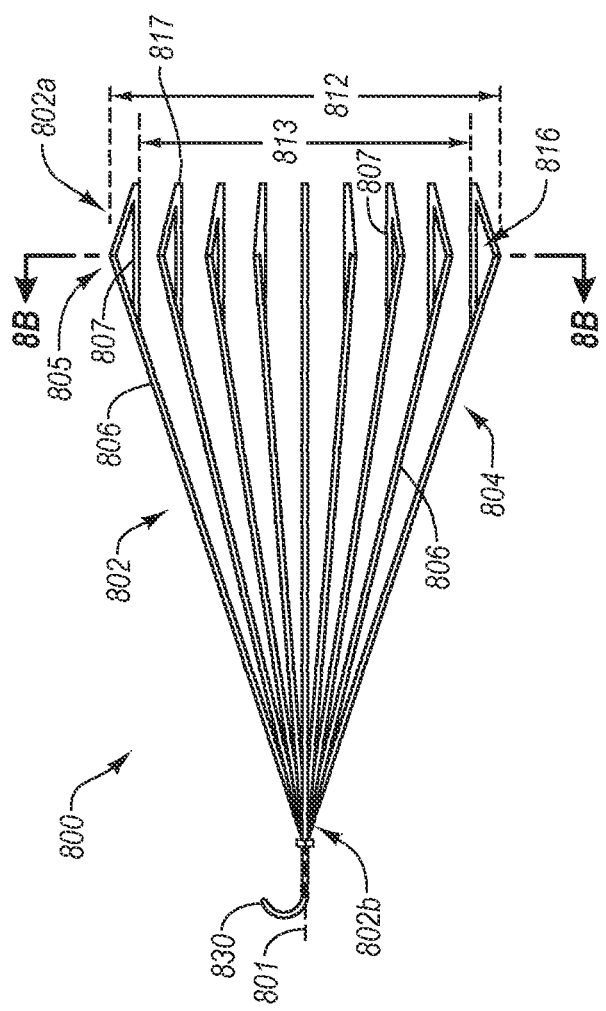
Fig. 8A
Fig. 8B

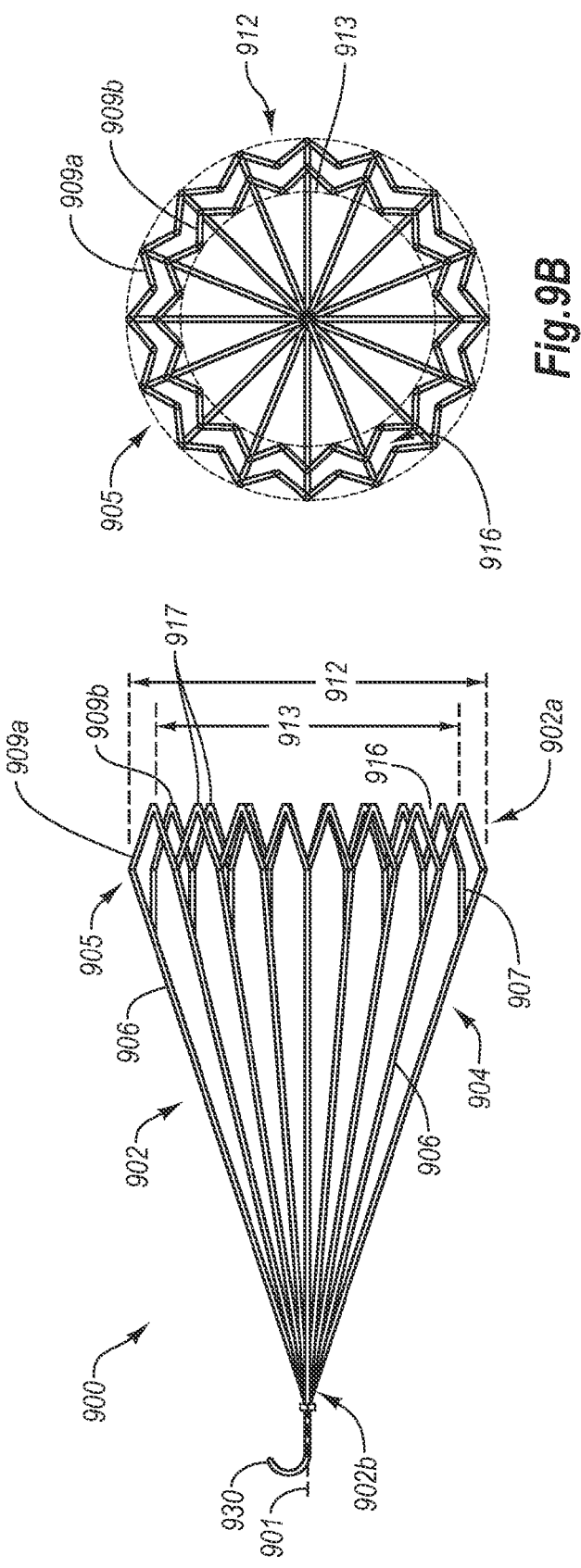

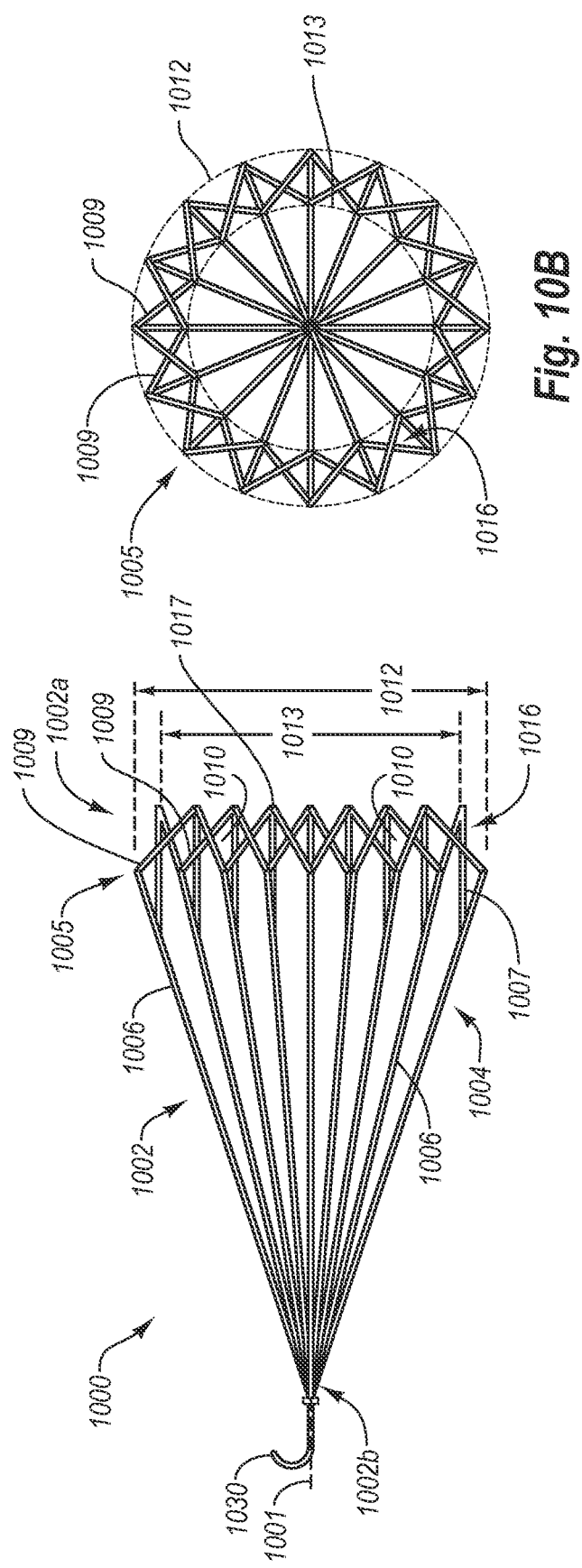

IMPLANTABLE LUMEN FILTER WITH ENHANCED DURABILITY

CROSS-REFERENCE TO RELATED APPLICATIONS

This Patent Application is a U.S. National Stage of International Application No. PCT/US2009/068287, filed Dec. 16, 2009, which claims the benefit of and priority to U.S. Provisional Patent Application having Ser. No. 61/138,470, filed on Dec. 17, 2008, the disclosures of which are incorporated herein by reference in their entireties.

FIELD OF THE INVENTION

The present invention relates generally to medical devices. More particularly the present invention relates to an implantable lumen filter with enhanced durability.

BACKGROUND OF THE INVENTION

Vein thrombosis is a medical condition wherein a blood clot, or thrombus, has formed inside a vein. Such a clot often develops in the calves, legs, or lower abdomen, but can also affect other veins in the body. The clot may partially or completely block blood flow, and may break off and travel through the bloodstream. Commonly, the clot is caused by a pooling of blood in the vein, often when an individual is bed-ridden for an abnormally long duration of time, for example, when resting following surgery or suffering from a debilitating illness, such as a heart attack or traumatic injury. However, there are many other situations that cause the formation of a blood clot.

Vein thrombosis is a serious problem because of the danger that the clot may break off and travel through the bloodstream to the lungs, causing a pulmonary embolism. A pulmonary embolism is an obstruction of the pulmonary artery or one of its branches by a blood clot or other foreign substance. A pulmonary embolism can be caused by a blood clot which migrated into the pulmonary artery or one of its branches.

This is similar to a blockage of the blood supply to the lungs that causes severe hypoxia and cardiac failure, and frequently results in death. For many patients, anti-coagulant drug therapies may be sufficient to dissipate the clots. For example, patients may be treated with anticoagulants such as heparin and with thrombolytic agents such as streptokinase.

Unfortunately, some patients may not respond to such drug therapy or may not tolerate such therapy. Also, there may be other reasons why an anticoagulant is not desirable. For example, patients may have an acute sensitivity to heparin or may suffer from prolonged internal and/or external bleeding as a result of such drug therapies. Also, such drug therapies simply may be ineffective in preventing recurrent pulmonary emboli. In such circumstances, surgical procedures are required to prevent pulmonary emboli. Methods for prevention of primary or recurrent pulmonary emboli when anticoagulation therapies are ineffective are well-defined in the prior art. The current standard of therapy for prevention of pulmonary emboli in patients who are classified high-risk or are unable to be anticoagulated is percutaneous insertion and placement of an inferior vena cava filter device.

Vena cava filters are devices which are implanted in the inferior vena cava, providing a mechanical barrier to undesirable particulates. The filters may be used to filter peripheral venous blood clots and other particulates, which if remaining in the blood stream can migrate into the pulmonary artery or one of its branches and cause harm.

Vena cava filters can filter the blood stream by catching and collecting particulates within the blood stream. However, the basket-like shape of the filter may cause the particulates to congregate or collect near the center of the blood stream. This can result in an occlusion within the inferior vena cava, particularly as the amount of particulates builds within the vena cava filter. Not only can this reduce the usable lifespan of the filter, but it can also potentially cause serious harm to the patient.

Therefore, an implantable lumen filter with an enhanced durability and methods for filtering a body lumen may be useful.

BRIEF DESCRIPTION OF THE DRAWINGS

In order to describe the manner in which the above-recited and other advantages and features of the invention can be obtained, a more particular description of the invention briefly described above will be rendered by reference to specific configurations thereof which are illustrated in the appended drawings. Understanding that these drawings depict only typical configurations of the invention and are not therefore to be considered to be limiting of its scope, the invention will be described and explained with additional specificity and detail through the use of the accompanying drawings.

FIGS. 1A-B illustrate an example implantable lumen filter.

FIGS. 2A-B illustrate another example implantable lumen filter.

FIGS. 3A-B illustrate a further example implantable lumen filter.

FIGS. 4A-B illustrate a still further example implantable lumen filter.

FIGS. 5A-B illustrate a yet further example implantable lumen filter.

FIGS. 6A-B illustrate another example implantable lumen filter.

FIGS. 8A-B illustrate a still further example implantable lumen filter.

FIGS. 9A-B illustrate a yet further example implantable lumen filter.

FIGS. 10A-B illustrate another example implantable lumen filter.

Figure 7B:
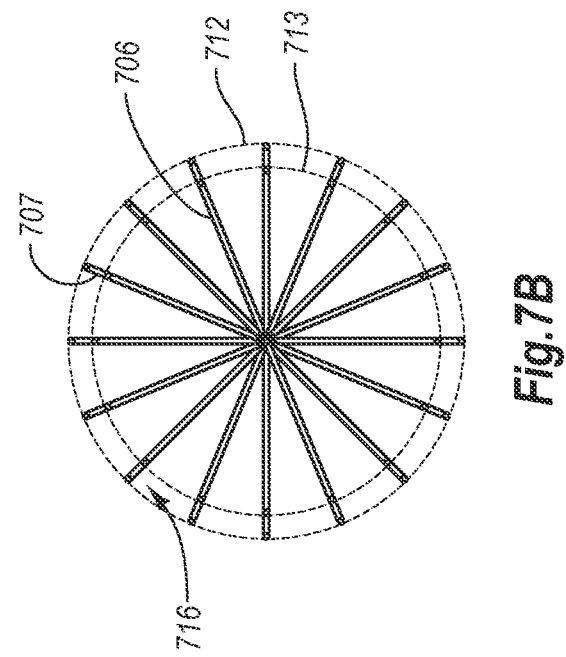
FIGS. 7A-B illustrate a further example implantable lumen filter.

It should be noted that the figures are not drawn to scale and that elements of similar structures or functions are generally represented by like reference numerals for illustrative purposes throughout the figures. It also should be noted that the figures are only intended to facilitate the description of example configurations of the present invention.

DETAILED DESCRIPTION

The configurations described herein extend generally to an implantable lumen filter with enhanced durability and methods for filtering a body lumen. By way of example only, a body lumen may include a blood vessel. Filtering of the body lumen may be performed by implantable lumen filters. For instance, configurations of implantable lumen filters (e.g. including vena cava and/or other lumen filters), are described. Components of implantable filters also are described.

Some implantable lumen filters may be designed to capture, inhibit, and/or lyse particulates of a particular size within the lumen. Many implantable lumen filters may be generally tapered from a distal end toward a proximal end. For example, implantable lumen filters may be generally cone shaped. As a result of their shape, many implantable lumen filters may direct particulates towards and capture the particulates within a central portion of the lumen. As particulates collect within the filter near the center of the lumen, flow within the lumen, such as blood flow, is disrupted and/or reduced. This can lead to an occlusion thereby reducing the usable lifespan of the filter and potentially causing harm to a patient.

Example implantable lumen filters described herein may be configured to direct particulates within a lumen radially outwardly and/or to collect particulates proximate an inner wall of the lumen. By so doing, the example implantable lumen filters described herein can reduce or eliminate obstructions within the central portion of the lumen. As a result, these implantable lumen filters can have longer usable lifespans and enhanced safety characteristics.

The example implantable lumen filters described herein may be manufactured from any suitable material. For example, an implantable lumen filter may be at least partially formed from various materials including nickel titanium and/or alloys thereof, cobalt chromium alloys and/or alloys thereof, other materials, and/or combinations thereof. These materials may include at least one beneficial agent incorporated into the material and/or coated over at least a portion of the material.

The beneficial agents may be applied to implantable lumen filters that have been coated with a polymeric compound. Incorporation of the compound or drug into the polymeric coating of the implantable lumen filter can be carried out by dipping the polymer-coated implantable lumen filter into a solution containing the compound or drug for a sufficient period of time (such as, for example, five minutes) and then drying the coated implantable lumen filter, such as by way of air drying for a sufficient period of time (such as, for example, 30 minutes). The polymer-coated implantable lumen filter containing the beneficial agent may then be delivered to a body vessel.

The pharmacologic agents that can be effective in preventing restenosis can be classified into the categories of anti-proliferative agents, anti-platelet agents, anti-inflammatory agents, anti-thrombotic agents, and thrombolytic agents. Anti-proliferative agents may include, for example, crystalline rapamycin. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v \beta 3$, antibodies that block binding to gpIIaIIIb or $\alpha v \beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

One or more immunosuppressant agents may be used. Immunosuppressant agents may include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAM tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins. In addition, a crystalline rapamycin analog, A-94507, SDZ RAD (a.k.a. Everolimus), and/or other immunosuppressants.

FIGS. 1A-B illustrate an example implantable lumen filter 100 according to some configurations. In FIG. 1A, the implantable lumen filter 100 is shown in flattened form for ease of discussion. FIG. 1B illustrates an end view of the implantable lumen filter 100 of FIG. 1A. The implantable lumen filter 100 may include a body 102 having a proximal end 102a and a distal end 102b. The proximal end 102a may be the end of the body 102 that is typically opposite to the end typically advanced first into a body lumen to deploy the implantable lumen filter 100. In other configurations, the proximal end 102a may be the end of the body 102 that is first disposed within a body lumen. The body 102 may be transitionable from a compressed state toward an expanded state and is shown in FIGS. 1A-B in the expanded state. The implantable lumen filter 100 may also include one or more retrieval portions 130a, 130b coupled to the body 102 for retrieving the body 102 from a lumen.

The body 102 of the example implantable lumen filter 100 may include an outer surface 104 defined by a plurality of outer struts 106. The body 102 may include a proximal portion 103a and a distal portion 103b. The proximal portion 103a of the body 102 may include a proximal outer surface 104a defined by a plurality of proximal outer struts 106a. In the illustrated configuration, the proximal outer struts 106a each extend from the proximal end 102a toward an apex 105. At least some of the plurality of struts 106a can extend generally in alignment with a longitudinal axis 101. As used herein, the term "extend generally in alignment with a longitudinal axis" means to extend generally along a plane that contains the longitudinal axis. The proximal outer surface 104a may have a generally tapered shape from the apex 105 to the proximal end 102a. As used herein, a generally tapered shape may include a line and/or curve tapered toward and rotated about a longitudinal axis 101, a generally right circular conical outer surface, a generally oblique conic outer surface, and/or other shapes that generally taper toward the one end.

The distal portion 103b may include a distal outer surface 104b defined by a plurality of distal outer struts 106b. In the illustrated configuration, the distal outer struts 106b extend longitudinally from the distal end 102b toward the apex 105 and can be generally in alignment with the longitudinal axis 101. The distal outer surface 104b may have a generally tapered shape from the apex 105 to the distal end 102b.

The implantable lumen filter 100 may be generally narrower near the proximal end 102a and distal end 102b with the apex 105 of the body 102 being a generally wider portion of the implantable lumen filter 100. The apex 105 may operate to anchor the implantable lumen filter 100 against the inner wall of a lumen. For example, in its expanded/deployed state, the body 102 may have an outer dimension 112 at or near the apex 105 which is similar to the inner dimension of the lumen wall.

The apex 105 may be configured to engage an inner surface of the body lumen. The surface area and/or other features of the apex 105 may be determined to facilitate engagement of the inner wall of the body lumen. The apex 105 may also impart a radial force to an inner surface of a body lumen. The apex 105 may impart a radial force sufficient to anchor the implantable lumen filter 100 without piercing an inner surface of the body lumen.

The apex 105 may be dimensioned and configured to generally align the implantable lumen filter 100 within a body lumen. The apex 105 may facilitate alignment within the body lumen by controlling the surface area of the implantable lumen filter 100 to be in contact with the body lumen, by increasing the radial force applied by the implantable lumen filter 100, by other features, and/or combinations of the same.

The apex 105, in the illustrated configuration, may include a generally angular shape in the outer surface 104. In further configurations, however, the apex 105 may be less angular and more rounded or planar. Near the apex 105, the outer surface 104 can vary more in its shape than the remainder of the outer surface 104, such as the proximal outer surface 104a or the distal outer surface 104b, which may include a more constant surface shape that tapers from the apex 105 to the proximal end 102a or the distal end 102b.

The body 102 may also include a first longitudinal dimension 114 and a second longitudinal dimension 115. The first longitudinal dimension 114 may extend from the proximal end 102a to the apex 105 generally parallel with the longitudinal axis 101 and represent the longitudinal length of the proximal portion 103a. The second longitudinal dimension 115 may extend from the distal end 102b to the apex 105 generally parallel with the longitudinal axis 101 and represent the longitudinal length of the distal portion 103b. The first longitudinal dimension 114 and second longitudinal dimension 115 may be substantially equal or may differ with the first longitudinal dimension 114 being longer or shorter than the second longitudinal dimension 115.

The outer struts 106 of the body 102 may be formed from various materials including nickel titanium and/or alloys thereof, cobalt chromium and/or alloys thereof, other materials, and/or combinations thereof. At least one beneficial agent may be incorporated into the material of and/or coated over at least a portion of the outer struts 106. In configurations where the body 102 is not defined by outer struts 106, the structure defining the body 102 may be formed from these various materials and/or may have at least one beneficial agent incorporated into the material of and/or coated over at least a portion of the material. For instance, an anti-thrombotic beneficial agent may be coated over at least a portion of the body 102.

The outer struts 106 may be welded and/or otherwise connected together to form the body 102. For example, the body 102 may be formed by welding or otherwise connecting the proximal outer struts 106a and distal outer struts 106b together. In particular, the distal ends of the proximal outer struts 106a can be connected to the corresponding proximal ends of the distal outer struts 106b to form the body 102. In addition, the connection between the proximal outer struts 106a and distal outer struts 106b may at least partially define the apex 105 in the outer surface 104. In a further configuration, one or more outer struts 106 may extend as single pieces from the proximal end 102a to the distal end 102b and include bends and/or other features to define the apex 105.

The proximal outer struts 106a may also be welded or otherwise connected together at the proximal end 102a, while the distal outer struts 106b may be welded or otherwise connected together at the distal end 106b. In other configurations, the outer struts 106 may be formed by removing material from the body 102 using, for example, laser cutting, etching, machining, grinding, and/or other suitable material removing procedures.

The outer struts 106 may form a plurality of apertures 110 in the body 102. In the configuration illustrated in FIGS. 1A-B, the example outer struts 106 form generally elongated V-shaped apertures extending between adjacent outer struts 106 from the proximal end 102a and distal end 102b to the apex 105, the apertures 110 defining wider openings near the apex 105 and narrower openings near the proximal and distal ends 102a, 102b, respectively. The number of outer struts 106 can be selectively determined to produce a desired spacing between adjacent outer struts 106 and a corresponding aperture 110 size and shape. In further configurations, the outer struts 106 may form apertures 110 having other shapes, such as diamond shapes, triangular shapes, chevron shapes, polygonal shapes, and/or other suitable shapes. In some configurations, the outer struts 106 may form apertures 110 that are generally the same shape. In other configurations, the outer struts 106 may form apertures 110 that are different shapes and/or varying shapes.

The apertures 110 may be spread across various locations of the body 102. The size and/or number of apertures 110 may vary and may be selected to inhibit passage of and/or to lyse particulates of a selected size while allowing blood components smaller than the selected size to pass through said apertures.

The apertures 110 can be selectively configured to allow a particulate of a particular size to pass through the body 102. For example, in the example implantable lumen filter 100 of FIGS. 1A-B, the outer struts 106 can be selectively spaced as desired to define the size and/or shape of the apertures 110 so as to only allow passage of particulates smaller than a selected size. The number of outer struts 106 included in the implantable lumen filter 100 can be increased or decreased as desired to increase or decrease the size and/or shape of the apertures 110.

In further configurations, the size and/or shape of apertures 110 located within the proximal portion 103a may differ from the size and/or shape of apertures 110 located within the distal portion 103b. In addition, the positions of apertures 110 may vary from the proximal portion 103a to the distal portion 103b as desired. Furthermore, the number of proximal outer struts 106a of the proximal portion 103a may be larger or smaller than the number of distal outer struts 106b of the distal portion 103b.

The proximal portion 103a and distal portion 103b may be generally symmetrical about a plane defined by the apex 105. For example, the proximal and distal portions 103a, 103b can each incorporate a substantially conical shape with the tip end of the cone being located at the proximal and distal ends 102a, 102b, respectively, and with the wider base portion of the cone being located at or near the apex 105. In further configurations, the size and/or shape of the proximal portion 103a can differ from the size and/or shape of the distal portion 103b.

The implantable lumen filter 100 can be configured to direct particulates within a body lumen in a radially-outward direction. In particular, the body 102 of the implantable lumen filter 100 may be shaped, sized, and/or oriented to facilitate direction of particulates within the lumen towards the outer dimension 112 of the body 102 and/or inner surface of a lumen wall.

In one example configuration, the implantable lumen filter 100 can be deployed within a body lumen such that the proximal portion 103a is located on the upstream side of the implantable lumen filter 100. The proximal portion 103a can be configured to direct particulates flowing within the lumen radially outward. In particular, the particulates can be directed by the proximal outer surface 104a towards the outer dimension 112 of the body 102. For instance, when a particulate collides with the proximal outer surface 104a, the proximal outer struts 106a can deflect the particulate towards the lumen wall. In addition, particulates may travel along the longitudinally extending proximal outer struts 106a until they either reach an aperture 110 in the body 102 large enough to pass through the body, become lysed into smaller particulates small enough to pass through the body 102, become collected between the proximal outer surface 104a and a lumen wall, become collected by one or more outer struts 106a, and/or combinations of the same.

Accordingly, the example implantable lumen filter 100 can direct particulates towards and cause particulates to be collected near the outer dimension 112 of the body 102 and/or the inner surface of the lumen wall. As a result, some aspects of the example implantable lumen filter 100 can limit or prevent blockage of the central portion of a lumen, thereby maintaining flow within the lumen for a longer period of time. Thus, the example implantable lumen filter 100 disclosed in FIGS. 1A-B can enhance the lifespan, durability, and safety of the implantable lumen filter 100.

In a further embodiment, the implantable lumen filter 100 can be interchangeably deployed within a lumen. For example, the implantable lumen filter 100 can be deployed with either the distal end 102b or the proximal end 102a positioned on the upstream side of the implantable lumen filter 100 within the lumen.

Once a particulate is collected by the implantable lumen filter 100, one or more beneficial agents can be introduced into the lumen flow in order to further break down and/or lyse the particulate. For example, the beneficial agent(s) can break the particulate down into smaller particulates that are able to pass through the apertures 110. As a result, very few or no particulates may remain collected upon the implantable lumen filter 100 when it is retrieved from the lumen.

Alternatively, particulates may remain collected by the implantable lumen filter 100 until the implantable lumen filter 100 is removed from the lumen. In particular, the implantable lumen filter 100 may be removed in such a way so as to effectively collect any particulates released into the flow of the lumen when the implantable lumen filter 100 disengages the lumen wall. For example, a retrieval apparatus (e.g., 1263, FIG. 12F) used to retrieve the implantable lumen filter 100 from a lumen may include a particulate collector that extends from the retrieval apparatus and abuts a lumen wall downstream from the deployed position of the implantable lumen filter 100. If particulates are released as the implantable lumen filter 100 is retrieved from the lumen, the particulates can be collected within the particulate collector and then removed from the lumen along with the retrieval apparatus.

The implantable lumen filter 100 may incorporate at least one component of the implantable lumen filters 200, 300, 400, 500, 600, 700, 800, 900, 1000, 1100, and 1200 described in connection with FIGS. 2-12, respectively. The following non-limiting list of examples indicates the interchangeability of at least some of the components of the implantable lumen filters 100, 200, 300, 400, 500, 600, 700, 800, 900, 1000, 1100, and 1200 described herein. For instance, the implantable lumen filter 100 can include one or more inner struts (e.g., 207, 707, 807, 907, and 1007, as shown in FIGS. 2 and 7-10, respectively) in addition to the plurality of outer struts 106. In another example, the implantable lumen filter 100 may further incorporate one or more rings of struts (e.g., 409, 909, and 1009, as shown in FIGS. 4 and 9-10, respectively).

FIGS. 2A-B illustrate another example implantable lumen filter 200. In FIG. 2A, the implantable lumen filter 200 is shown in flattened form for ease of discussion. FIG. 2B illustrates a cross-sectional view of the implantable lumen filter 200 along the line 2B-2B shown in FIG. 2A. The example implantable lumen filter 200 of this configuration may be functionally similar to the example implantable lumen filter 100 previously described above and shown in FIGS. 1A-B in most respects, wherein certain features will not be described in relation to this configuration wherein those components may function in the manner as described above and are hereby incorporated into this additional configuration described below. Like structures and/or components are given like reference numerals. Additionally, the implantable lumen filter 200 may incorporate at least one component of the implantable lumen filters 100, 300, 400, 500, 600, 700, 800, 900, 1000, 1100, and 1200 described in connection with FIGS. 1 and 3-12, respectively.

The implantable lumen filter 200 may include a body 202 having a proximal end 202a and a distal end 202b. The proximal end 202a may be the end of the body 202 that is closest to a user as the implantable lumen filter 200 is advanced into a body lumen. In other configurations, the proximal end 202a may be the end of the body 202 that is farthest from a user. The body 202 may be transitionable from a compressed state toward an expanded state and is shown in the FIGS. 2A-B in the expanded state. The implantable lumen filter 200 may also include one or more retrieval portions 230a, 230b coupled to the body 202 for retrieving the body 202 from a lumen.

The body 202 of the example implantable lumen filter 200 may include an outer surface 204 defined by a plurality of outer struts 206. The body 202 may include a proximal portion 203a and a distal portion 203b. The proximal portion 203a of the body 202 may include a proximal outer surface 204b defined by a plurality of proximal outer struts 206a. In the illustrated configuration, the proximal outer struts 206a extend longitudinally from the proximal end 202a toward an apex 205. At least some of the plurality of outer struts 206a extend generally in alignment with a longitudinal axis 201. The proximal outer surface 204a, in the illustrated configuration, may have a generally tapered shape from the apex 205 to the proximal end 202a.

The distal portion 203b may include a distal outer surface 204b defined by a plurality of distal outer struts 206b. In the illustrated configuration, the distal outer struts 206b extend longitudinally from the distal end 202b toward the apex 205 generally in alignment with the longitudinal axis 201. The distal outer surface 204b, in the illustrated configuration, may have a generally tapered shape from the apex 205 to the distal end 202b.

The implantable lumen filter 200 may be generally narrower near the proximal end 202a and distal end 202b with the apex 205 of the body 202 being a generally wider portion of the implantable lumen filter 200. The apex 205 may operate to anchor the implantable lumen filter 200 against the inner wall of a lumen. For example, in its expanded/deployed state, the body 202 may have an outer dimension 212 at or near the apex 205 which is similar to the inner dimension of the lumen wall.

The apex 205 may be configured to engage an inner surface of the body lumen. The surface area and/or other features of the apex 205 may be determined to facilitate engagement of the inner wall of the body lumen. The apex 205 may also facilitate alignment within the body lumen by controlling the surface area of the implantable lumen filter 200 to be in contact with the body lumen, by increasing the radial force applied by the implantable lumen filter 200, by other features, and/or combinations of the same.

The apex 205, in the illustrated configuration, may include a generally angular shape. In further configurations, however, the apex 205 may be less angular and more rounded or planar. Near the apex 205, the outer surface 204 is typically more varying in its shape than the remainder of the outer surface 204, such as the proximal outer surface 204a or the distal outer surface 204b, which typically include a more constant surface shape that tapers from the proximal end 202a or from the distal end 202b towards the apex 205.

The example implantable lumen filter 200 also may include a plurality of inner struts 207. The plurality of inner struts 207 may attach to and extend from one or more outer struts 206. At least some of the plurality of inner struts 207 may extend longitudinally, generally in parallel with the longitudinal axis 201. In further configurations, one or more inner struts 207 may extend in any direction within the body 202 in order to achieve a desired result. The plurality of inner struts 207 may define an inner dimension 213. The outer dimension 212 and inner dimension 213 may define an annular region 216 extending around the body 202. The plurality of inner struts 207 may be configured to inhibit and/or lyse particulates flowing within or near the annular region 216.

The inner dimension 213 can vary with respect to the outer dimension 212 as desired according to multiple configurations. For example, the inner dimension 213 can range from about 5% to about 95% of the outer dimension 212. In a further example, the inner dimension 213 can range from about 25% to about 75% of the outer dimension 212. In an even further example, the inner dimension 213 can be about half of the outer dimension 212.

The body 202 may also include a first longitudinal dimension 214 and a second longitudinal dimension 215. The first longitudinal dimension 214 may extend from the proximal end 202a to the apex 205 generally parallel with the longitudinal axis 201 and represent the longitudinal length of the proximal portion 203a. The second longitudinal dimension 215 may extend from the distal end 202b to the apex 205 generally parallel with the longitudinal axis 201 and represent the longitudinal length of the distal portion 203b. The first longitudinal dimension 214 and second longitudinal dimension 215 may be substantially equal or may differ with the first longitudinal dimension 214 being longer or shorter than the second longitudinal dimension 215.

The struts 206, 207 may be formed from various materials including nickel titanium and/or alloys thereof, cobalt chromium and/or alloys thereof, other materials, and/or combinations thereof. At least one beneficial agent may be incorporated into the material of and/or coated over at least a portion of the outer struts 206. In configurations where the body 202 is not defined by outer struts 206, the structure defining the body 202 may be formed from these various materials and/or may have at least one beneficial agent incorporated into the material of and/or coated over at least a portion of the material. For instance, an anti-thrombotic beneficial agent may be coated over at least a portion of the body 202.

The outer struts 206 may be welded and/or otherwise connected together to form the body 202. For example, the body 202 may be formed by welding or otherwise connecting the proximal outer struts 206a and distal outer struts 206b together. In particular, the distal ends of the proximal outer struts 206a can be connected to the corresponding proximal ends of the distal outer struts 206b to form the body 202. In addition, the connection between the proximal outer struts 206a and distal outer struts 206b may at least partially define the apex 205 in the outer surface 204. In a further configuration, one or more outer struts 206 may extend as single pieces from the proximal end 202a to the distal end 202b and include bends and/or other features to define the apex 205.

The inner struts 207 may be welded or otherwise connected to the outer struts 206. For example, the inner struts 207 can be connected at one end to the distal outer struts 206b and at the other end to the proximal outer struts 206a. In addition, the inner struts 207 can be connected to the distal outer struts 206b and/or the proximal outer struts 206a at any point along the lengths of the distal outer struts 206b and proximal outer struts 206a. In the illustrated configuration, the inner struts 207 span the apex 205, being connected at the ends to the outer struts 206, the connections to the outer struts 206 being spaced a distance from the apex 205.

The proximal outer struts 206a may also be welded or otherwise connected together at the proximal end 202a, while the distal outer struts 206b may be welded or otherwise connected together at the distal end 206b. In other configurations, the outer struts 206 may be formed by removing material from the body 202 using, for example, laser cutting and/or other material removing procedures.

The outer struts 206 may form a plurality of apertures 210 in the body 202. In the configuration illustrated in FIGS. 2A-B, the example outer struts 206 form generally elongated, V-shaped apertures 210 extending between the outer struts 206 from the proximal end 202a and distal end 202b to the apex 205, the apertures 210 defining wider openings near the apex 205 and narrower openings near the proximal and distal ends 202a, 202b, respectively. The number of outer struts 206 can be selectively determined to produce a desired spacing between adjacent outer struts 206 and a corresponding aperture 210 size and shape. In further configurations, the outer struts 206 may form apertures 210 having other shapes, such as diamond shapes, triangular shapes, chevron shapes, and/or other suitable shapes.

The proximal portion 203a and distal portion 203b may be generally symmetrical about a plane defined by the apex 205. For example, the proximal and distal portions 203a, 203b can each incorporate a substantially conical shape with the tip end of the cone being located at the proximal and distal ends 202a, 202b respectively, and with the wider base portion of the cone being located at or near the apex 205. In further configurations, the size and/or shape of the proximal portion 203a can differ from the size and/or shape of the distal portion 203b.

The implantable lumen filter 200 can be configured to direct particulates within a body lumen in a radially-outward direction. In particular, the body 202 of the implantable lumen filter 200 may be shaped, sized, and/or oriented to facilitate direction of particulates within the lumen towards the outer dimension 212 of the body 202 and/or an inner surface of a lumen wall.

In one example configuration, the implantable lumen filter 200 can be deployed within a body lumen such that the proximal portion 203a is located on the upstream side of the implantable lumen filter 200. The proximal portion 203a can be configured to direct particulates flowing within the lumen radially outward. In particular, the particulates can be directed by the proximal outer surface 204a towards the outer dimension 212 of the body 202. For instance, when a particulate collides with the proximal outer surface 204a, the proximal outer struts 206a can deflect the particulate towards the lumen wall. Particulates may also travel along the proximal outer struts 206a until they either reach an aperture in the body 202 large enough to pass through the body 202, become lysed into smaller particulates small enough to pass through the body 202, become collected between the proximal outer surface 204a and the lumen wall, become collected by one or more outer struts 206a, become collected within the annular region 216, and/or combinations of the same.

Accordingly, the example implantable lumen filter 200 can direct particulates towards and cause particulates to be collected near the outer dimension 212 and/or within the annular region 216 of the body 202. As a result, some aspects of the example implantable lumen filter 200 can limit or prevent blockage of the central portion of a lumen, thereby maintaining flow within the lumen for a longer period of time. Thus, the example implantable lumen filter 200 disclosed in FIGS. 2A-B can enhance the lifespan and durability of the implantable lumen filter 200.

In a further embodiment, the implantable lumen filter 200 can be interchangeably deployed within a lumen. For example, the implantable lumen filter 200 can be deployed with either the distal end 202b or the proximal end 202a positioned on the upstream side of the implantable lumen filter 200 within the lumen.

FIGS. 3A-B illustrate a further configuration of an implantable lumen filter 300. In FIG. 3A, the implantable lumen filter 300 is shown in flattened form for ease of discussion. FIG. 3B illustrates a cross-sectional view of the implantable lumen filter 300 of FIG. 3A along the line 3B-3B. The implantable lumen filter 300 of this further configuration may be functionally similar to the implantable lumen filters 100, 200 previously described above and shown in FIGS. 1-2 in most respects, wherein certain features will not be described in relation to this configuration wherein those components may function in the manner as described above and are hereby incorporated into this additional configuration described below. Like structures and/or components are given like reference numerals. Additionally, the implantable lumen filter 300 may incorporate at least one component of the implantable lumen filters 100, 200, 400, 500, 600, 700, 800, 900, 1000, 1100, and 1200 described in connection with FIGS. 1-2 and 4-12, respectively.

The implantable lumen filter 300 may include a body 302 having a proximal end 302a and a distal end 302b. The proximal end 302a may be the end of the body 302 that is closest to a user as the implantable lumen filter 300 is advanced into a body lumen. In other configurations, the proximal end 302a may be the end of the body 302 that is farthest from a user. The body 302 may be transitionable from a compressed state toward an expanded state and is shown in the FIGS. 3A-B in the expanded state. The implantable lumen filter 300 may also include one or more retrieval portions 330a, 330b coupled to the body 302 for retrieving the body 302 from a lumen.

The body 302 of the example implantable lumen filter 300 may include an outer surface 304 defined by a plurality of outer struts 306. The body 302 may include a proximal portion 303a and a distal portion 303b. The proximal portion 303a of the body 302 may include a proximal outer surface 304b defined by a plurality of proximal outer struts 306a. In the illustrated configuration, the proximal outer struts 306a extend longitudinally from the proximal end 302a toward an apex 305 generally in alignment with the longitudinal axis 301. The proximal outer surface 304a, in the illustrated configuration, may have a generally tapered shape from the proximal end 302a to the apex 305.

The distal portion 303b may include a distal outer surface 304b defined by a plurality of outer struts 306b. In the illustrated configuration, the distal outer struts 306b extend longitudinally from the distal end 302b toward the apex 305 generally in alignment with the longitudinal axis 301. The distal outer surface 304b, may have a generally tapered shape from the distal end 302b to the apex 305.

The example implantable lumen filter 300 may also include a plurality of overhanging outer struts 306c. The overhanging outer struts 306c may be connected to the body 302 proximate the apex 305 and extend in alignment with the longitudinal axis 301 towards the proximal end 302a, overhanging at least a portion of the proximal outer surface 304a. The overhanging outer struts 306c may at least partially define an outer dimension 312 and an annular region 316 extending around the body 302a at or near the apex 305 of the body 302. The annular region 316 may be configured to collect and/or inhibit particulates flowing within the lumen.

The proximal outer struts 306a may at least partially define an inner dimension 313 of the annular region 316. The inner dimension 313 can vary with respect to the outer dimension 312 as desired according to multiple configurations. For example, the inner dimension 313 can range from about 5% to about 95% of the outer dimension 312. In a further example, the inner dimension 313 can range from about 25% to about 75% of the outer dimension 312. In an even further example, the inner dimension 313 can be about half of the outer dimension 312.

The implantable lumen filter 300 may be generally narrower near the proximal end 302a and distal end 302b with the apex 305 of the body 302 being a generally wider portion of the implantable lumen filter 300. The apex 305 may operate to anchor the implantable lumen filter 300 against the inner wall of a lumen. For example, in its expanded/deployed state, the body 302 may have an outer dimension 312 at or near the apex 305 which is similar to an inner dimension of the lumen wall. The apex 305 may also import a radial force to an inner surface of the body lumen.

The body 302 may also include a first longitudinal dimension 314 and a second longitudinal dimension 315. The first longitudinal dimension 314 may extend from the proximal end 302a to the apex 305 generally parallel with the longitudinal axis 301 and represent the longitudinal length of the proximal portion 303a. The second longitudinal dimension 315 may extend from the distal end 302b to the apex 305 generally parallel with the longitudinal axis 301 and represent the longitudinal length of the distal portion 303b. The first longitudinal dimension 314 and second longitudinal dimension 315 may be substantially equal or may differ with the first longitudinal dimension 314 being longer or shorter than the second longitudinal dimension 315.

The struts 306 of the body 302 may be formed from various materials including nickel titanium and/or alloys thereof, cobalt chromium and/or alloys thereof, other materials, and/or combinations thereof. At least one beneficial agent may be incorporated into the material of and/or coated over at least a portion of the struts 306. In configurations where the body 302 is not defined by outer struts 306, the structure defining the body 302 may be formed from these various materials and/or may have at least one beneficial agent incorporated into the material of and/or coated over at least a portion of the material. For instance, an anti-thrombotic beneficial agent may be coated over at least a portion of the body 302.

The struts 306 may be welded and/or otherwise connected together to form the body 302. For example, the body 302 may be formed by welding or otherwise connecting the proximal outer struts 306a, distal outer struts 306b, and overhanging outer struts 306c together. In particular, the distal ends of the proximal outer struts 306a can be connected to the corresponding proximal ends of the distal outer struts 306b to form the body 302. In addition, the connection between the proximal outer struts 306a and distal outer struts 306b may at least partially define the apex 305 in the outer surface 304. In a further configuration, one or more outer struts 306 may extend as single pieces from the proximal end 302a to the distal end 302b and include bends and/or other features to at least partially define the apex 305.

The overhanging struts 306c may be welded or otherwise connected at one end to the distal outer struts 308b and/or the proximal outer struts 306a at or near the apex 305. In other configurations, the overhanging struts 306c may include portions of the distal outer struts 306b extending beyond their connection with the proximal outer struts 306a.

The proximal outer struts 306a may also be welded or otherwise connected together at the proximal end 302a, while the distal outer struts 306b may be welded or otherwise connected together at the distal end 306b. In other configurations, the outer struts 306 may be formed by removing material from the body 302 using, for example, laser cutting and/or other material removing procedures.

The outer struts 306 may form a plurality of apertures 310 in the body 302. In the configuration illustrated in FIGS. 3A-B, the example outer struts 306 form generally elongated, V-shaped apertures extending between the outer struts 306 from the proximal end 302a and distal end 302b to the apex 305, the apertures 310 defining wider openings near the apex 305 and narrower openings near the proximal and distal ends 302a, 302b, respectively. The number of outer struts 306 can be selectively determined to produce a desired spacing between adjacent outer struts 306 and a corresponding aperture 310 size and shape. In further configurations, the outer struts 306 may form apertures 310 having other shapes, such as diamond shapes, triangular shapes, chevron shapes, and/or other suitable shapes.

The proximal portion 303a and distal portion 303b may be generally symmetrical about a plane defined by the apex 305. For example, the proximal and distal portions 303a, 303b can each incorporate a substantially conical shape with the tip end of the cone being located at the proximal and distal ends 302a, 302b respectively, and with the wider base portion of the cone being located at or near the apex 305. In further configurations, the size and/or shape of the proximal portion 303a can differ from the size and/or shape of the distal portion 303b.

The implantable lumen filter 300 may be configured to direct particulates within a body lumen in a radially-outward direction. In particular, the body 302 of the implantable lumen filter 300 may be shaped, sized, and/or oriented to facilitate direction of particulates within the lumen towards the outer dimension 312 and/or annular region 316 of the body 302 and/or the inner surface of a lumen wall.

In one example configuration, the implantable lumen filter 300 can be deployed within a body lumen with the proximal portion 303a located on the upstream side of the implantable lumen filter 300. The proximal portion 303a can direct particulates flowing within the lumen radially outward. In particular, the particulates can be directed by the proximal outer surface 304a so as to collect proximate the apex 305 and/or within the annular region 316 of the body 302. For instance, when a particulate collides with the proximal outer surface 304a, the proximal outer struts 306a can deflect the particulate towards the lumen wall. Particulates may also travel along the longitudinally extending outer struts 306a until they either reach an aperture in the body 302 large enough to pass through the body, become lysed into smaller particulates small enough to pass through the body 302, become collected between the proximal outer surface 304a and the lumen wall, become collected by one or more outer struts 306a, become collected within or rear the annular region 316, and/or combinations of the same.

Accordingly, the example implantable lumen filter 300 can direct particulates towards and cause particulates to be collected near the outer dimension 312 and/or within the annular region 316 of the body 302. As a result, some aspects of the example implantable lumen filter 300 can limit or prevent blockage of the central portion of a lumen, thereby maintaining flow within the lumen. Thus, the example implantable lumen filter 300 disclosed in FIGS. 3A-B can enhance the lifespan and durability of the implantable lumen filter 300.

In a further embodiment, the implantable lumen filter 300 can be interchangeably deployed within a lumen. For example, the implantable lumen filter 300 can be deployed with either the distal end 302b or the proximal end 302a positioned on the upstream side of the implantable lumen filter 300 within the lumen.

The overhanging struts 303c may enhance the retention of particulates collected upon the implantable lumen filter 300 while the implantable lumen filter 300 is retrieved from a lumen. For example, as the implantable lumen filter 300 is elongated and the apex 305 disengages the lumen wall, the overhanging struts 303c may function to retain collected particulates within the annular region 316, thereby preventing the collected particulates from flowing past the implantable lumen filter 300 and back into the fluid flow of the lumen.

FIGS. 4A-B illustrate a still further configuration of an example implantable lumen filter 400. In FIG. 4A, the implantable lumen filter 400 is shown in flattened form for ease of discussion. FIG. 4B illustrates an end view of the implantable lumen filter 400 of FIG. 4A. The implantable lumen filter 400 of this further configuration may be functionally similar to the example implantable lumen filters 100, 200, 300 previously described above and shown in FIGS. 1-3 in most respects, wherein certain features will not be described in relation to this configuration wherein those components may function in the manner as described above and are hereby incorporated into this additional configuration described below. Like structures and/or components are given like reference numerals. Additionally, the implantable lumen filter 400 may incorporate at least one component of the implantable lumen filters 100, 200, 300, 500, 600, 700, 800, 900, 1000, 1100, and 1200 described in connection with FIGS. 1-3 and 5-12, respectively.

The implantable lumen filter 400 may include a body 402 having a proximal end 402a and a distal end 402b. The proximal end 402a may be the end of the body 402 that is closest to a user as the implantable lumen filter 400 is advanced into a body lumen. In other configurations, the proximal end 402a may be the end of the body 402 that is farthest from a user. The body 402 may be transitionable from a compressed state toward an expanded state and is shown in the FIGS. 4A-B in the expanded state. The implantable lumen filter 400 may also include one or more retrieval portions 430a, 430b coupled to the body 402 for retrieving the body 402 from a lumen.

The body 402 of the example implantable lumen filter 400 may include an outer surface 404 defined by a plurality of outer struts 406. The body 402 may include a proximal portion 403a and a distal portion 403b. The proximal portion 403a of the body 402 may include a proximal outer surface 404b defined by a plurality of proximal outer struts 406a. In the illustrated configuration, at least some of the proximal outer struts 406a extend longitudinally from the proximal end 402a toward an apex 405 in the outer surface 404 of the body 402. The proximal outer surface 404a, in the illustrated configuration, may have a generally tapered shape from the apex 405 to the proximal end 402a.

A portion of the plurality of proximal outer struts 406b may form one or more rings 409 extending around the proximal outer surface 404a. The one or more rings 409 may at least partially define an outer dimension 412, an inner dimension 413, and/or an annular region 416 at or near the apex 405 in the outer surface 404 of the body 402. The inner dimension 413 can vary with respect to the outer dimension 412 as desired according to multiple configurations. For example, the inner dimension 413 can range from about 5% to about 95% of the outer dimension 412. In a further example, the inner dimension 413 can range from about 25% to about 75% of the outer dimension 412. In an even further example, the inner dimension 413 can be about half of the outer dimension 412.

The one or more rings 409 may include one or more points 417. The points 417 may be configured to inhibit, lyse, and/or impale particulates flowing within a lumen. As shown in the illustrated configuration, the points 417 can be angled inward toward the longitudinal axis 401. In a further example, the points 417 can be angled in any direction desired, such as in parallel with the longitudinal axis 401 or outward towards the apex 405.

The distal portion 403b may include a distal outer surface 404b defined by a plurality of outer struts 406b. In the illustrated configuration, at least some of the distal outer struts 406b extend longitudinally from the distal end 402b toward the apex 405 generally in alignment with the longitudinal axis 401. The distal outer struts 406b may also form on or more rings 409 extending around the distal outer surface 404b. The distal outer surface 404b, in the illustrated configuration, may have a generally tapered shape from the apex 405 to the distal end 402b.

The implantable lumen filter 400 may be generally narrower near the proximal end 402a and distal end 402b with the apex 405 of the body 402 being a generally wider portion of the implantable lumen filter 400. The apex 405 may operate to anchor the implantable lumen filter 400 against an inner wall of a lumen. For example, in its expanded/deployed state, the body 402 may have an outer dimension 412 at or near the apex 405 which is similar to an inner dimension of the lumen wall. The apex 405 may also impart a radial force to an inner surface of the body lumen.

The body 402 may also include a first longitudinal dimension 414 and a second longitudinal dimension 415. The first longitudinal dimension 414 may extend from the proximal end 402a to the apex 405 generally parallel with the longitudinal axis 401 and represent the longitudinal length of the proximal portion 403a. The second longitudinal dimension 415 may extend from the distal end 402b to the apex 405 generally parallel with the longitudinal axis 401 and represent the longitudinal length of the distal portion 403b. The first longitudinal dimension 414 and second longitudinal dimension 415 may be substantially equal or may differ with the first longitudinal dimension 414 being longer or shorter than the second longitudinal dimension 415.

The outer struts 406 of the body 402 may be formed from various materials including nickel titanium and/or alloys thereof, cobalt chromium and/or alloys thereof, other materials, and/or combinations thereof. At least one beneficial agent may be incorporated into the material of and/or coated over at least a portion of the outer struts 406. In configurations where the body 402 is not defined by outer struts 406, the structure defining the body 402 may be formed from these various materials and/or may have at least one beneficial agent incorporated into the material of and/or coated over at least a portion of the material. For instance, an anti-thrombotic beneficial agent may be coated over at least a portion of the body 402.

The outer struts 406 may be welded and/or otherwise connected together to form the body 402. For example, the body 402 may be formed by welding or otherwise connecting the distal outer struts 406b and the proximal outer struts 406a together. In addition, one or more outer struts 406 may be connected together to form the rings 409. In a further configuration, one or more outer struts 406 may extend as single pieces from the proximal end 402a to the distal end 402b and include bends and/or other features to define the apex 405.

The proximal outer struts 406a may also be welded or otherwise connected together at the proximal end 402a, while the distal outer struts 406b may be welded or otherwise connected together at the distal end 406b. In other configurations, the outer struts 406 may be formed by removing material from the body 402 using, for example, laser cutting and/or other material removing procedures.

The outer struts 406 may form a plurality of apertures 410 in the body 402. In the configuration illustrated in FIGS. 4A-B, the example outer struts 406 form generally elongated, V-shaped apertures extending between the outer struts 406 from the proximal end 402a and distal end 402b to near the apex 405, the apertures 410 defining wider openings near the apex 405 and narrower openings near the proximal and distal ends 402a, 402b, respectively. The number of outer struts 406 can be selectively determined to produce a desired spacing between adjacent outer struts 406 and a corresponding aperture 410 size and shape. In addition, the rings 409 may form differently shaped apertures 410 in the annular region 416 of the body 402. In further configurations, the outer struts 406 may form apertures 410 having other shapes, such as diamond shapes, triangular shapes, chevron shapes, and/or other suitable shapes.

The proximal portion 403a and distal portion 403b may be generally symmetrical about a plane defined by the apex 405. For example, the proximal and distal portions 403a, 403b can each incorporate a substantially conical shape with the tip end of the cone being located at the proximal and distal ends 402a, 402b respectively, and with the wider base portion of the cone being located at or near the apex 405. In further configurations, the size and/or shape of the proximal portion 403a can differ from the size and/or shape of the distal portion 403b.

The implantable lumen filter 400 can be configured to direct particulates within a body lumen in a radially-outward direction. In particular, the body 402 of the implantable lumen filter 400 may be shaped, sized, and/or oriented to facilitate direction of particulates within the lumen towards the outer dimension 412 and/or annular region 416 of the body 402 and/or a lumen wall.

In one example configuration, the implantable lumen filter 400 can be deployed within a body lumen such that the proximal portion 403a is located on the upstream side of the implantable lumen filter 400. The proximal portion 403a can be configured to direct particulates flowing within the lumen radially outward. In particular, the particulates can be directed by the proximal outer surface 404a so as to collect proximate the outer dimension 412 of the body 402. For instance, when a particulate collides with the proximal outer surface 404a, the proximal outer struts 406a can deflect the particulate towards the lumen wall. Particulates may also travel along the longitudinally extending outer struts 406a until they either reach an aperture in the body 402 large enough to pass through the body, become lysed into smaller particulates small enough to pass through the body 402, become collected between the proximal outer surface 404a and the lumen wall, become collected by one or more outer struts 406a, become collected within the annular region 416, and/or combinations of the same.

Accordingly, the example implantable lumen filter 400 can direct particulates towards and cause particulates to be collected near the outer dimension 412 and/or within the annular region 416 of the body 402. As a result, some aspects of the example implantable lumen filter 400 can limit or prevent blockage of the central portion of a lumen, thereby maintaining flow within the lumen. Thus, the example implantable lumen filter 400 disclosed in FIGS. 4A-B can enhance the lifespan and durability of the implantable lumen filter 400.

In a further embodiment, the implantable lumen filter 400 can be interchangeably deployed within a lumen. For example, the implantable lumen filter 400 can be deployed with either the distal end 402b or the proximal end 402a positioned on the upstream side of the implantable lumen filter 400 within the lumen.

FIGS. 5A-B illustrate a yet further configuration of an implantable lumen filter 500. In FIG. 5A, the implantable lumen filter 500 is shown in flattened form for ease of discussion. FIG. 5B illustrates an end view of the implantable lumen filter 500 of FIG. 5A. The implantable lumen filter 500 of this other configuration may be functionally similar to the implantable lumen filters 100, 200, 300, 400 previously described above and shown in FIGS. 1-4 in most respects, wherein certain features will not be described in relation to this configuration wherein those components may function in the manner as described above and are hereby incorporated into this additional configuration described below. Like structures and/or components are given like reference numerals. Additionally, the implantable lumen filter 500 may incorporate at least one component of the implantable lumen filters 100, 200, 300, 400, 600, 700, 800, 900, 1000, 1100, and 1200 described in connection with FIGS. 1-4 and 6-12, respectively.

The implantable lumen filter 500 may include a body 502 having a proximal end 502a and a distal end 502b. The proximal end 502a may be the end of the body 502 that is closest to a user as the implantable lumen filter 500 is advanced into a body lumen. In other configurations, the proximal end 502a may be the end of the body 502 that is farthest from a user. The body 502 may be transitionable from a compressed state toward an expanded state and is shown in the FIGS. 5A-B in the expanded state. The implantable lumen filter 500 may also include one or more retrieval portions 530a, 530b coupled to the body 502 for retrieving the body 502 from a lumen.

The body 502 of the example implantable lumen filter 500 may include an outer surface 504 defined by a plurality of outer struts 506. The body 502 may include a proximal portion 503a and a distal portion 503b. The proximal portion 503a of the body 502 may include a proximal outer surface 504b defined by a plurality of proximal outer struts 506a. In the illustrated configuration, portions of the proximal outer struts 506a extend longitudinally from the proximal end 502a toward an apex 505 generally in alignment with the longitudinal axis 501. In addition, further portions of the proximal outer struts 506a can be bent and/or angled in a direction away from parallel with the longitudinal axis 501. The proximal outer surface 504a, in the illustrated configuration, may have a generally tapered shape from the proximal end 502a to the apex 505.

The angled portions 506a' of the proximal outer struts 506a may at least partially define an outer dimension 512, an inner dimension 513, and an annular region 516 at or near the apex 505 of the body 502. The inner dimension 513 can vary with respect to the outer dimension 512 as desired according to multiple configurations. For example, the inner dimension 513 can range from about 5% to about 95% of the outer dimension 512. In a further example, the inner dimension 513 can range from about 25% to about 75% of the outer dimension 512. In an even further example, the inner dimension 513 can be about half of the outer dimension 512.

The distal portion 503b may include a distal outer surface 504b defined by a plurality of outer struts 506b. In the illustrated configuration, the distal outer struts 506b extend longitudinally from the distal end 502b toward the apex 505 generally in alignment with the longitudinal axis 501. The distal outer surface 504b, in the illustrated configuration, may have a generally tapered shape from the distal end 502b to the apex 505.

The implantable lumen filter 500 may be generally narrower near the proximal end 502a and distal end 502b with the apex 505 of the body 502 being a generally wider portion of the implantable lumen filter 500. The apex 505 may operate to anchor the implantable lumen filter 500 against an inner wall of a lumen. For example, in its expanded/deployed state, the body 502 may have an outer dimension 512 at or near the apex 505 which is similar to the inner dimension of the lumen wall. The apex 505 may also impart a radial force to an inner surface of the body lumen.

The body 502 may also include a first longitudinal dimension 514 and a second longitudinal dimension 515. The first longitudinal dimension 514 may extend from the proximal end 502a to the apex 505 generally parallel with the longitudinal axis 501 and represent the longitudinal length of the proximal portion 503a. The second longitudinal dimension 515 may extend from the distal end 502b to the apex 505 generally parallel with the longitudinal axis 501 and represent the longitudinal length of the distal portion 503b. The first longitudinal dimension 514 and second longitudinal dimension 515 may be substantially equal or may differ with the first longitudinal dimension 514 being longer or shorter than the second longitudinal dimension 515.

The outer struts 506 of the body 502 may be formed from various materials including nickel titanium and/or alloys thereof, cobalt chromium and/or alloys thereof, other materials, and/or combinations thereof. At least one beneficial agent may be incorporated into the material of and/or coated over at least a portion of the outer struts 506. In configurations where the body 502 is not defined by outer struts 506, the structure defining the body 502 may be formed from these various materials and/or may have at least one beneficial agent incorporated into the material of and/or coated over at least a portion of the material. For instance, an anti-thrombotic beneficial agent may be coated over at least a portion of the body 502.

The outer struts 506 may be welded and/or otherwise connected together to form the body 502. For example, the body 502 may be formed by welding or otherwise connecting the proximal outer struts 506a and distal outer struts 506b together. In particular, the distal ends of the proximal outer struts 506a can be connected to the corresponding proximal ends of the distal outer struts 506b to form the body 502. In addition, the connection between the proximal outer struts 506a and distal outer struts 506b may at least partially define the apex 505 in the outer surface 504. In a further configuration, one or more outer struts 506 may extend as single pieces from the proximal end 502a to the distal end 502b and include bends and/or other features to define the apex 505.

The proximal outer struts 506a may also be welded or otherwise connected together at the proximal end 502a, while the distal outer struts 506b may be welded or otherwise connected together at the distal end 506b. In other configurations, the outer struts 506 may be formed by removing material from the body 502 using, for example, laser cutting and/or other material removing procedures.

The outer struts 506 may form a plurality of apertures 510 in the body 502. In the configuration illustrated in FIGS. 5A-B, the example outer struts 506 form generally elongated, V-shaped apertures extending between the outer struts 506 from the proximal end 502a and distal end 502b towards the apex 505, the apertures 510 defining wider openings near the apex 505 and narrower openings near the proximal and distal ends 502a, 502b, respectively. The number of outer struts 506 can be selectively determined to produce a desired spacing between adjacent outer struts 506 and a corresponding aperture 510 size and shape. In further configurations, the outer struts 506 may form apertures 510 having other shapes, such as diamond shapes, triangular shapes, chevron shapes, and/or other suitable shapes.

The proximal portion 503a and distal portion 503b may be generally symmetrical about a plane defined by the apex 505. For example, the proximal and distal portions 503a, 503b can each incorporate a substantially conical shape with the tip end of the cone being located at the proximal and distal ends 502a, 502b respectively, and with the wider base portion of the cone being located at or near the apex 505. In further configurations, the size and/or shape of the proximal portion 503a can differ from the size and/or shape of the distal portion 503b.

The implantable lumen filter 500 can be configured to direct particulates within a body lumen in a radially-outward direction. In particular, the body 502 of the implantable lumen filter 500 may be shaped, sized, and/or oriented to facilitate direction of particulates within the lumen towards the outer dimension 512 of the body 502 and/or a lumen wall.

In one example configuration, the implantable lumen filter 500 can be deployed within a body lumen with the proximal portion 503a being located on the upstream side of the implantable lumen filter 500. The proximal portion 503a can be configured to direct particulates flowing within the lumen radially outward. In particular, the particulates can be directed by the proximal outer surface 504a so as to collect proximate the outer dimension 512 of the body 502. For instance, when a particulate collides with the proximal outer surface 504a, the proximal outer struts 506a can deflect the particulate towards the lumen wall. Particulates may travel along the longitudinally extending outer struts 506a until they either reach an aperture in the body 502 large enough to pass through the body, become lysed into smaller particulates small enough to pass through the body 502, become collected between the proximal outer surface 504a and the lumen wall, become collected by one or more outer struts 506a, become collected within or near the annular region 516, and/or combinations of the same.

Accordingly, the example implantable lumen filter 500 can direct particulates towards and cause particulates to be collected near the outer dimension 512 and/or within the annular region 516 of the body 502. As a result, some aspects of the example implantable lumen filter 500 can limit or prevent blockage of the central portion of a lumen, thereby maintaining flow within the lumen for a longer period of time. Thus, the example implantable lumen filter 500 disclosed in FIGS. 5A-B can enhance the lifespan and durability of the implantable lumen filter 500.

In a further embodiment, the implantable lumen filter 500 can be interchangeably deployed within a lumen. For example, the implantable lumen filter 500 can be deployed with either the distal end 502b or the proximal end 502a positioned on the upstream side of the implantable lumen filter 500 within the lumen.

FIGS. 6A-B illustrate another configuration of an implantable lumen filter 600. In FIG. 6A, the implantable lumen filter 600 is shown in flattened form for ease of discussion. FIG. 6B illustrates a cross-sectional view of the implantable lumen filter 600 of FIG. 6A along the line 6B-6B. The implantable lumen filter 600 of this other configuration may be functionally similar to the implantable lumen filters 100, 200, 300, 400, 500 previously described above and shown in FIGS. 1-5 in most respects, wherein certain features will not be described in relation to this configuration wherein those components may function in the manner as described above and are hereby incorporated into this additional configuration described below. Like structures and/or components are given like reference numerals. Additionally, the implantable lumen filter 600 may incorporate at least one component of the implantable lumen filters 100, 200, 300, 400, 500, 700, 800, 900, 1000, 1100, and 1200 described in connection with FIGS. 1-5 and 7-12, respectively.

The implantable lumen filter 600 may include a body 602 having a proximal end 602a and a distal end 602b. The proximal end 602a may be the end of the body 602 that is closest to a user as the implantable lumen filter 600 is advanced into a body lumen. In other configurations, the proximal end 602a may be the end of the body 602 that is farthest from a user. The body 602 may be transitionable from a compressed state toward an expanded state and is shown in the FIGS. 6A-B in the expanded state. The implantable lumen filter 600 may also include one or more retrieval portions 630a, 630b coupled to the body 602 for retrieving the body 602 from a lumen.

The body 602 of the example implantable lumen filter 600 may include an outer surface 604 defined by a plurality of outer struts 606. The body 602 may include a proximal portion 603a and a distal portion 603b. The proximal portion 603a of the body 602 may include a proximal outer surface 604b defined by a plurality of proximal outer struts 606a. In the illustrated configuration, the proximal outer struts 606a extend longitudinally from the proximal end 602a toward an apex 605 generally in alignment with the longitudinal axis 601. The proximal outer surface 604a, in the illustrated configuration, may have a generally tapered shape from the proximal end 602a to the apex 605.

The distal portion 603b may include a distal outer surface 604b defined by a plurality of outer struts 606b. In the illustrated configuration, the distal outer struts 606b extend longitudinally from the distal end 602b toward the apex 605 generally in alignment with the longitudinal axis 601. The distal outer surface 604b, in the illustrated configuration, may have a generally tapered shape from the distal end 602b to the apex 605.

The example implantable lumen filter 600 may also include a plurality of overhanging outer struts 606c. The overhanging outer struts 606c may be located proximate, and may at least partially define the apex 605. The overhanging outer struts 606c can angle outwards and overhang at least a portion of the proximal outer surface 604a. The overhanging outer struts 606c may at least partially define an outer dimension 612 and an annular region 616 extending around the body 602 at or near the apex 605. The annular region 616 may be configured to collect and/or inhibit particulates flowing within the lumen. In one example configuration, the overhanging struts 606c may be formed by portions of the distal outer struts 606b overhanging a connection with the proximal outer struts 606a.

The proximal outer struts 606a may at least partially define an inner dimension 613 of the annular region 616. The inner dimension 613 can vary with respect to the outer dimension 612 as desired according to multiple configurations. For example, the inner dimension 613 can range from about 5% to about 95% of the outer dimension 612. In a further example, the inner dimension 613 can range from about 25% to about 75% of the outer dimension 612. In an even further example, the inner dimension 613 can be about half of the outer dimension 612.

The implantable lumen filter 600 may be generally narrower near the proximal end 602a and distal end 602b with the apex 605 of the body 602 being a generally wider portion of the implantable lumen filter 600. The apex 605 may operate to anchor the implantable lumen filter 600 against an inner wall of a lumen. For example, in its expanded/deployed state, the body 602 may have an outer dimension 612 at or near the apex 605 which is similar to the inner dimension of the lumen wall.

The body 602 may also include a first longitudinal dimension 614 and a second longitudinal dimension 615. The first longitudinal dimension 614 may extend from the proximal end 602a to the apex 605 generally parallel with the longitudinal axis 601 and represent the longitudinal length of the proximal portion 603a. The second longitudinal dimension 615 may extend from the distal end 602b to the apex 605 generally parallel with the longitudinal axis 601 and represent the longitudinal length of the distal portion 603b. The first longitudinal dimension 614 and second longitudinal dimension 615 may be substantially equal or may differ with the first longitudinal dimension 614 being longer or shorter than the second longitudinal dimension 615.

The outer struts 606 of the body 602 may be formed from various materials including nickel titanium and/or alloys thereof, cobalt chromium and/or alloys thereof, other materials, and/or combinations thereof. At least one beneficial agent may be incorporated into the material of and/or coated over at least a portion of the outer struts 606. In configurations where the body 602 is not defined by outer struts 606, the structure defining the body 602 may be formed from these various materials and/or may have at least one beneficial agent incorporated into the material of and/or coated over at least a portion of the material. For instance, an anti-thrombotic beneficial agent may be coated over at least a portion of the body 602.

The overhanging struts 606c may be welded or otherwise connected at one end to the distal outer struts 608b and/or the proximal outer struts 606a at or near the apex 605. In other configuration, the overhanging struts 606c may include portions of the distal outer struts 606b extending beyond their connection with the proximal outer struts 606a.

The proximal outer struts 606a may also be welded or otherwise connected together at the proximal end 602a, while the distal outer struts 606b may be welded or otherwise connected together at the distal end 606b. In other configurations, the outer struts 606 may be formed by removing material from the body 602 using, for example, laser cutting and/or other material removing procedures.

The outer struts 606 may form a plurality of apertures 610 in the body 602. In the configuration illustrated in FIGS. 6A-B, the example outer struts 606 form generally elongated, V-shaped apertures extending between the outer struts 606 from the proximal end 602a and distal end 602b to the apex 605, the apertures 610 defining wider openings near the apex 605 and narrower openings near the proximal and distal ends 602a, 602b, respectively. The number of outer struts 606 can be selectively determined to produce a desired spacing between adjacent outer struts 606 and a corresponding aperture 610 size and shape. In further configurations, the outer struts 606 may form apertures 610 having other shapes, such as diamond shapes, triangular shapes, chevron shapes, and/or other suitable shapes.

The proximal portion 603a and distal portion 603b may be generally symmetrical about a plane defined by the apex 605. For example, the proximal and distal portions 603a, 603b can each incorporate a substantially conical shape with the tip end of the cone being located at the proximal and distal ends 602a, 602b respectively, and with the wider base portion of the cone being located at or near the apex 605. In further configurations, the size and/or shape of the proximal portion 603a can differ from the size and/or shape of the distal portion 603b.

The implantable lumen filter 600 may be configured to direct particulates within a body lumen in a radially-outward direction. In particular, the body 602 of the implantable lumen filter 600 may be shaped, sized, and/or oriented to facilitate direction of particulates within the lumen towards the outer dimension 612 and/or annular region 616 of the body 602 and/or the inner surface of a lumen wall.

In one example configuration, the implantable lumen filter 600 can be deployed within a body lumen with the proximal portion 603a being located on the upstream side of the implantable lumen filter 600. The proximal portion 603a can direct particulates flowing within the lumen radially outward. In particular, the particulates can be directed by the proximal outer surface 604a towards the apex 605 and/or the annular region 616 of the body 602. For instance, when a particulate collides with the proximal outer surface 604a, the proximal outer struts 606a can deflect the particulate radially outward. Particulates may also travel along the longitudinally extending outer struts 606a until they either reach an aperture in the body 602 large enough to pass through the body, become lysed into smaller particulates small enough to pass through the body 602, become collected between the proximal outer surface 604a and the lumen wall, become collected by one or more outer struts 606a, become collected within the annular region 616, and/or combinations of the same.

Accordingly, the example implantable lumen filter 600 can direct particulates towards and cause particulates to be collected near the outer dimension 612 and/or within the annular region 616 of the body 602. As a result, some aspects of the example implantable lumen filter 600 can limit or prevent blockage of the central portion of a lumen, thereby maintaining flow within the lumen. Thus, the example implantable lumen filter 600 disclosed in FIGS. 6A-B can enhance the lifespan and durability of the implantable lumen filter 600.

In a further embodiment, the implantable lumen filter 600 can be interchangeably deployed within a lumen. For example, the implantable lumen filter 600 can be deployed with either the distal end 602b or the proximal end 602a positioned on the upstream side of the implantable lumen filter 600 within the lumen.

The overhanging struts 603c may enhance the retention of particulates collected upon the implantable lumen filter 600 while the implantable lumen filter 600 is retrieved from a lumen. For example, as the implantable lumen filter 600 is elongated and the apex 605 disengages the lumen wall, the overhanging struts 603c may function to retain collected particulates within the annular region 616, thereby preventing the collected particulates from flowing past the implantable lumen filter 600 and back into the fluid flow of the lumen.

Figure 7A:
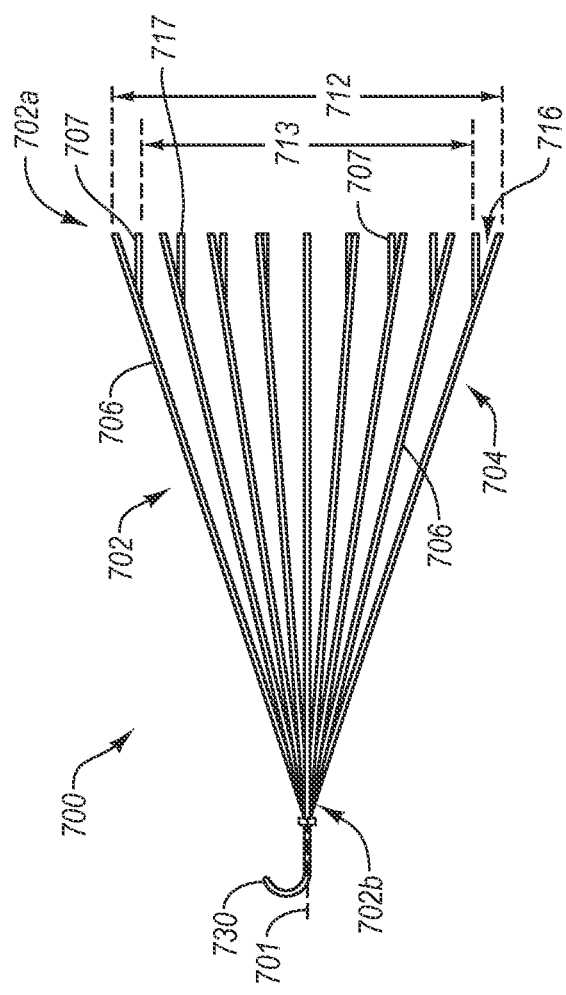

FIGS. 7A-B illustrate another configuration of an implantable lumen filter 700. In FIG. 7A, the implantable lumen filter 700 is shown in flattened form for ease of discussion. FIG. 7B illustrates an end view of the implantable lumen filter 700 of FIG. 7A. The implantable lumen filter 700 of this other configuration may be functionally similar to the implantable lumen filters 100, 200, 300, 400, 500, 600 previously described above and shown in FIGS. 1-6 in most respects, wherein certain features will not be described in relation to this configuration wherein those components may function in the manner as described above and are hereby incorporated into this additional configuration described below. Like structures and/or components are given like reference numerals. Additionally, the implantable lumen filter 700 may incorporate at least one component of the implantable lumen filters 100, 200, 300, 400, 500, 600, 800, 900, 1000, 1100, and 1200 described in connection with FIGS. 1-6 and 8-12, respectively.

The implantable lumen filter 700 is shown in flattened form for ease of discussion. The implantable lumen filter 700 may include a body 702 having a proximal end 702a and a distal end 702b. The proximal end 702a may be the end of the body 702 that is closest to a user as the implantable lumen filter 700 is advanced into a body lumen. In other configurations, the proximal end 702a may be the end of the body 702 that is farthest from a user. The body 702 may be transitionable from a compressed state toward an expanded state and is shown in the FIGS. 7A-B in the expanded state. The implantable lumen filter 700 may also include one or more retrieval portions 730 coupled to the body 702 for retrieving the body 702 from a lumen.

The body 702 may define an outer surface 704 being defined by a plurality of struts 706. The outer surface 704, in the illustrated configuration, may have a generally tapered shape from the proximal end 702a toward the distal end 702b. A generally tapered shape may include a line and/or curve tapered toward and rotated about a longitudinal axis 701, a generally right circular conic outer surface, a generally oblique conic outer surface, and/or other shapes that generally taper toward the one end.

The distal end 702b, in the illustrated configuration, may be a generally more narrow portion of the implantable lumen filter 700 with the proximal end 702a being a generally wider portion of the implantable lumen filter 700. Alternatively, the distal end 702b may be a generally wider portion of the implantable lumen filter 700 with the proximal end 702a being a more narrow portion of the implantable lumen filter 700.

The implantable lumen filter 700 may also include a plurality of inner struts 707 extending inwards from the plurality of outer struts 706. For example, the inner struts 707 may be attached to the outer struts 706 a distance away from the proximal end 702a and extend towards the proximal end 702a. The plurality of inner struts 707 may form one or more points 717. The points 717 may be configured to inhibit, lyse, and/or impale particulates flowing within a lumen. The inner struts 707 can extend in a direction generally parallel with the longitudinal axis 701, or can be angled in any direction desired for a particular application. In addition, the number of inner struts 707 included in the body 702, and the position and number of inner struts 707 attached to each outer strut 706 can be varied as desired for each particular application.

The outer struts 706 may define, near the proximal end 702a, an outer dimension 712 of the body 702, while the inner struts 707 may define an inner dimension 713. The outer dimension 712 and inner dimension 713 may define an annular region 716 extending around the body 702 at or near the proximal end 702a. The inner dimension 713 can vary with respect to the outer dimension 712 as desired according to multiple configurations. For example, the inner dimension 713 can range from about 5% to about 95% of the outer dimension 712. In a further example, the inner dimension 713 can range from about 25% to about 75% of the outer dimension 712. In an even further example, the inner dimension 713 can be about half of the outer dimension 712.

The implantable lumen filter 700 may be configured to inhibit and/or collect particulates within the annular region 716. For example, particulates entering the implantable lumen filter 700 by way of the annular region 716 may be collected and/or retained within the annular region 716. As a result, at least a portion of the particulates collected by the implantable lumen filter 700 can be retained at or near the outer dimension of the body 702, thereby at least partially maintaining the flow through the central portion of the lumen. By so doing, aspects of the example implantable lumen filter 700 of FIGS. 7A-B can prevent or minimize blockage and/or reduced flow through the lumen, thereby extending the lifespan and enhancing the durability of the implantable lumen filter 700.

The struts 706, 707 of the body 702 may be formed from various materials including nickel titanium and/or alloys thereof, cobalt chromium and/or alloys thereof, other materials, and/or combinations thereof. At least one beneficial agent may be incorporated into the material of and/or coated over at least a portion of the struts 706, 707.

The struts 706, 707 may be welded and/or otherwise connected together. For example, the outer struts 706 may be welded together at the distal end 702b. In addition, the inner struts 707 may be welded to the corresponding outer struts 706 a predetermined distance from the proximal end 702a. In other configurations, the struts 706, 707 may be formed by removing material from the body 702 using, for example, laser cutting and/or other material removing procedures.

The struts 706 may form a plurality of apertures 710 in the body 702. In the configuration illustrated in FIGS. 7A-B, the struts 706, 707 form generally V-shaped apertures 710. The struts 706, 707 may form other shapes, such as diamond shapes, chevron shapes, triangular shapes, and/or other suitable shapes. The struts 706, 707 may form apertures 710, that are generally the same shape, for example generally V-shaped. In other configurations, the struts 706, 707 may form apertures 710 that are different shapes, for example generally V-shaped and generally chevron shaped. In further configurations, the apertures 710 may all be of varying shapes.

The apertures 710 may be spread across various portions of the body 702. The size and/or number of apertures 710 may vary and may be selected to inhibit passage of and/or to lyse particulates of a selected size while allowing blood components smaller than the selected size to pass through said apertures. For instance, a proximal portion of apertures 710 may include generally larger and/or fewer apertures 710 than an intermediate portion and/or distal portion. Such a configuration may capture and/or lyse a variety of particles. In other configurations, the apertures 710 may be distributed over more and/or fewer portions.

In a further embodiment, the implantable lumen filter 700 can be interchangeably deployed within a lumen. For example, the implantable lumen filter 700 can be deployed with either the distal end 702b or the proximal end 702a positioned on the upstream side of the implantable lumen filter 700 within the lumen.

FIGS. 8A-B illustrate another configuration of an implantable lumen filter 800. In FIG. 8A, the implantable lumen filter 800 is shown in flattened form for ease of discussion. FIG. 8B illustrates a cross-sectional view of the implantable lumen filter 800 of FIG. 8A along the line 8B-8B. The implantable lumen filter 800 of this other configuration may be functionally similar to the implantable lumen filters 100, 200, 300, 400, 500, 600, 700 previously described above and shown in FIGS. 1-7 in most respects, wherein certain features will not be described in relation to this configuration wherein those components may function in the manner as described above and are hereby incorporated into this additional configuration described below. Like structures and/or components are given like reference numerals. Additionally, the implantable lumen filter 800 may incorporate at least one component of the implantable lumen filters 100, 200, 300, 400, 500, 600, 700, 900, 1000, 1100, and 1200 described in connection with FIGS. 1-7 and 9-12, respectively.

The implantable lumen filter 800 is shown in flattened form for ease of discussion. The implantable lumen filter 800 may include a body 802 having a proximal end 802a and a distal end 802b. The proximal end 802a may be the end of the body 802 that is closest to a user as the implantable lumen filter 800 is advanced into a body lumen. In other configurations, the proximal end 802a may be the end of the body 802 that is farthest from a user. The body 802 may be transitionable from a compressed state toward an expanded state and is shown in the FIGS. 8A-B in the expanded state. The implantable lumen filter 800 may also include one or more retrieval portions 830 coupled to the body 802 for retrieving the body 802 from a lumen.

The body 802 may define an outer surface 804 being defined by a plurality of struts 806. The outer surface 804, in the illustrated configuration, may have a generally tapered shape from the proximal end 802a toward the distal end 802b. The body 802 may include an apex 805 at or near the proximal end 802a. The apex 805 may include an angular or otherwise curved bend in the outer struts 806 proximate the proximal end 802a. The apex 805 may be configured to engage the inner surface of a body lumen to anchor and/or align the body within the lumen.

The implantable lumen filter 800 may include a plurality of inner struts 807 spanning a portion of the outer struts 806 including the apex 805. For example, the inner struts 807 may be attached at one end to the outer struts 806 a distance away from the proximal end 802a and at the other end to the outer struts 806 at the proximal end 802a. The inner struts 807 can extend in a direction generally parallel with the longitudinal axis 801, or can be angled in any direction desired for a particular application. In addition, the number of inner struts 807 included in the body 802, and the position and number of inner struts 807 attached to each outer strut 806 can be varied as desired for each particular application.

The apex 805 may define an outer dimension 812 of the body 802, while the inner struts 807 may at least partially define an inner dimension 813. The outer dimension 812 and inner dimension 813 may define an annular region 816 extending around the body 802 at or near the proximal end 802a. The inner dimension 813 can vary with respect to the outer dimension 812 as desired according to multiple configurations. For example, the inner dimension 813 can range from about 5% to about 95% of the outer dimension 812. In a further example, the inner dimension 813 can range from about 25% to about 75% of the outer dimension 812. In an even further example, the inner dimension 813 can be about half of the outer dimension 812.

The inner struts 807 and/or outer struts 808 may form one or more points 817. The points 817 may be configured to inhibit, lyse, and/or impale particulates flowing within a lumen. The points 817 can be configured to be angled in any direction desired. For example, the points can be angled inward toward the longitudinal axis 801. In further examples, the points 817 can be in parallel with the longitudinal axis 801 or angled outward towards the apex 805.

The implantable lumen filter 800 may be configured to inhibit and/or collect particulates within the annular region 816. For example, particulates entering the implantable lumen filter 800 by way of the annular region 816 may be collected and/or retained within the annular region 816. As a result, at least a portion of the particulates collected by the implantable lumen filter 800 can be retained at or near the outer dimension of the body 802, thereby at least partially maintaining the flow through the central portion of the lumen. By so doing, aspects of the example implantable lumen filter 800 of FIGS. 8A-B can reduce blockage of the lumen, thereby extending the lifespan and enhancing the durability of the implantable lumen filter 800.

In a further embodiment, the implantable lumen filter 800 can be interchangeably deployed within a lumen. For example, the implantable lumen filter 800 can be deployed with either the distal end 802b or the proximal end 802a positioned on the upstream side of the implantable lumen filter 800 within the lumen.

FIGS. 9A-B illustrate another configuration of an implantable lumen filter 900. In FIG. 9A, the implantable lumen filter 900 is shown in flattened form for ease of discussion. FIG. 9B illustrates an end view of the implantable lumen filter 900 of FIG. 9A. The implantable lumen filter 900 of this other configuration may be functionally similar to the implantable lumen filters 100, 200, 300, 400, 500, 600, 700, 800 previously described above and shown in FIGS. 1-8 in most respects, wherein certain features will not be described in relation to this configuration wherein those components may function in the manner as described above and are hereby incorporated into this additional configuration described below. Like structures and/or components are given like reference numerals. Additionally, the implantable lumen filter 900 may incorporate at least one component of the implantable lumen filters 100, 200, 300, 400, 500, 600, 700, 800, 1000, 1100, and 1200 described in connection with FIGS. 1-8 and 10-12, respectively.

The implantable lumen filter 900 is shown in flattened form for ease of discussion. The implantable lumen filter 900 may include a body 902 having a proximal end 902a and a distal end 902b. The proximal end 902a may be the end of the body 902 that is closest to a user as the implantable lumen filter 900 is advanced into a body lumen. In other configurations, the proximal end 902a may be the end of the body 902 that is farthest from a user. The body 902 may be transitionable from a compressed state toward an expanded state and is shown in the FIGS. 9A-B in the expanded state. The implantable lumen filter 900 may also include one or more retrieval portions 930 coupled to the body 902 for retrieving the body 902 from a lumen.

The body 902 may define an outer surface 904 being defined by a plurality of struts 906. The outer surface 904, in the illustrated configuration, may have a generally tapered shape from the proximal end 902a toward the distal end 902b. The body 902 may include an apex 905 at or near the proximal end 902a. The apex 905 may include an angular or otherwise curved bend in the outer struts 906 proximate the proximal end 902a. The apex 905 may be configured to engage the inner surface of a body lumen to anchor and/or align the body within the lumen.

The implantable lumen filter 900 may include a plurality of inner struts 907 extending from the outer struts 906. For example, the inner struts 907 may be attached to the outer struts 906 a distance away from the proximal end 902a. The inner struts 907 can extend in a direction generally parallel with the longitudinal axis 901, or can be angled in any direction desired for a particular application. In addition, the number of inner struts 907 included in the body 902, and the position and number of inner struts 907 attached to each outer strut 906 can be varied as desired for each particular application.

The outer struts 906 may include an outer ring 909a extending around the body 902 at or near the proximal end 902a and connecting the longitudinally-extending outer struts 906. The inner struts 907 may include by a corresponding inner ring 909b extending around and connecting the free ends of the inner struts 907.

The outer struts 906 and/or outer ring 909a may at least partially define an outer dimension 912 of the body 902, while the inner struts 907 and/or inner ring 909b may at least partially define an inner dimension 913. The outer dimension 912 and inner dimension 913 may define an annular region 916 at or near the proximal end 902a of the body 902. The inner dimension 913 can vary with respect to the outer dimension 912 as desired according to multiple configurations. For example, the inner dimension 913 can range from about 5% to about 95% of the outer dimension 912. In a further example, the inner dimension 913 can range from about 25% to about 75% of the outer dimension 912. In an even further example, the inner dimension 913 can be about half of the outer dimension 912.

The rings 909 may include one or more points 917. The points 917 may be configured to inhibit, lyse, and/or impale particulates flowing within a lumen. As shown in the illustrated configuration, the points 917 can be angled inward toward the longitudinal axis 901. In a further example, the points 917 can be angled in any direction desired, such as in parallel with the longitudinal axis 901 or outward towards the apex 905.

Aspects of the example implantable lumen filter 900 may be result in the inhibition or collection of particulates within the annular region 916. For example, particulates entering the implantable lumen filter 900 by way of the annular region 916 may be collected and/or retained within the annular region 916 by the outer struts 906, inner struts 907, and/or outer and inner rings 909a, 909b. As a result, at least a portion of the particulates collected by the implantable lumen filter 900 can be retained at or near the outer dimension of the body 902, thereby at least partially maintaining the flow through the central portion of the lumen. By so doing, aspects of the example implantable lumen filter 900 of FIGS. 9A-B can extend the lifespan and enhance the durability of the implantable lumen filter 900.

In a further embodiment, the implantable lumen filter 900 can be interchangeably deployed within a lumen. For example, the implantable lumen filter 900 can be deployed with either the distal end 902b or the proximal end 902a positioned on the upstream side of the implantable lumen filter 900 within the lumen.

FIGS. 10A-B illustrate another configuration of an implantable lumen filter 1000. In FIG. 10A, the implantable lumen filter 1000 is shown in flattened form for ease of discussion. FIG. 10B illustrates an end view of the implantable lumen filter 1000 of FIG. 10A. The implantable lumen filter 1000 of this other configuration may be functionally similar to the implantable lumen filters 100, 200, 300, 400, 500, 600, 700, 800, 1000 previously described above and shown in FIGS. 1-9 in most respects, wherein certain features will not be described in relation to this configuration wherein those components may function in the manner as described above and are hereby incorporated into this additional configuration described below. Like structures and/or components are given like reference numerals. Additionally, the implantable lumen filter 1000 may incorporate at least one component of the implantable lumen filters 100, 200, 300, 400, 500, 600, 700, 800, 900, 1100, and 1200 described in connection with FIGS. 1-9 and 11-12, respectively.

The implantable lumen filter 1000 is shown in flattened form for ease of discussion. The implantable lumen filter 1000 may include a body 1002 having a proximal end 1002a and a distal end 1002b. The proximal end 1002a may be the end of the body 1002 that is closest to a user as the implantable lumen filter 1000 is advanced into a body lumen. In other configurations, the proximal end 1002a may be the end of the body 1002 that is farthest from a user. The body 1002 may be transitionable from a compressed state toward an expanded state and is shown in the FIGS. 10A-B in the expanded state.

The implantable lumen filter 1000 may also include one or more retrieval portions 1030 coupled to the body 1002 for retrieving the body 1002 from a lumen.

The body 1002 may define an outer surface 1004 being defined by a plurality of outer struts 1006. The outer surface 1004, in the illustrated configuration, may have a generally tapered shape from the proximal end 1002a toward the distal end 1002b. The body 1002 may include an apex 1005 at or near the proximal end 1002a.

The body 1002 may include a plurality of inner struts 1007 extending from the outer struts 1006. For example, the inner struts 1007 may be attached at one end to the outer struts 1006 a distance away from the proximal end 1002a and at the other end to the outer struts 1006 at the proximal end 1002a. The inner struts 1007 can extend in a direction generally parallel with the longitudinal axis 1001, or can be angled in any direction desired for a particular application. In addition, the number of inner struts 1007 included in the body 1002, the size, shape, and/or length of each inner strut 1007, and the position and number of inner struts 1007 attached to each outer strut 1006 can be varied as desired for each particular application.

The outer struts 1006 may at least partially define an outer dimension 1012 of the body 1002, while the inner struts 1007 may at least partially define an inner dimension 1013. The outer dimension 1012 and inner dimension 1013 may define an annular region 1016 extending around the body 1002 at or near the proximal end 1002a. The inner dimension 1013 can vary with respect to the outer dimension 1012 as desired according to multiple configurations. For example, the inner dimension 1013 can range from about 5% to about 95% of the outer dimension 1012. In a further example, the inner dimension 1013 can range from about 25% to about 75% of the outer dimension 1012. In an even further example, the inner dimension 1013 can be about half of the outer dimension 1012.

The body 1002 may further include one or more rings 1009 at or near the proximal end 1002a. In the present example configuration, the rings 1009 can interconnect the plurality of outer struts 1006 and the plurality of inner struts. In addition, the rings 1009 can at least partially define the annular region 1016.

The rings 1009 may also form a plurality of apertures 1010 in the annular region 1016. In the configuration illustrated in FIGS. 10A-B, the rings 1009 form generally diamond shaped and triangular shaped apertures 1010. The rings 1009 and/or struts 1006, 1007 may also form apertures of other shapes.

The rings 1009 and/or inner struts 1007 may form one or more points 1017. The points 1017 may be configured to inhibit, lyse, and/or impale particulates flowing within a lumen. As shown in the illustrated configuration, the points 1017 can be angled inward toward the longitudinal axis 1001. In a further example, the points 1017 can be angled in any direction desired, such as in parallel with the longitudinal axis 1001 or outward towards the apex 1005.

The implantable lumen filter 1000 may be configured to inhibit and/or collect particulates within the annular region 1016. For example, particulates entering the implantable lumen filter 1000 by way of the annular region 1016 may be collected and/or retained within the annular region 1016. As a result, at least a portion of the particulates collected by the implantable lumen filter 1000 can be retained at or near the outer dimension of the body 1002, thereby at least partially maintaining the flow through the central portion of the lumen. By so doing, aspects of the example implantable lumen filter 1000 of FIGS. 10A-B can extend the lifespan and enhance the durability of the implantable lumen filter 1000.

In a further embodiment, the implantable lumen filter 1000 can be interchangeably deployed within a lumen. For example, the implantable lumen filter 1000 can be deployed with either the distal end 1002b or the proximal end 1002a positioned on the upstream side of the implantable lumen filter 1000 within the lumen.

Figure 11:
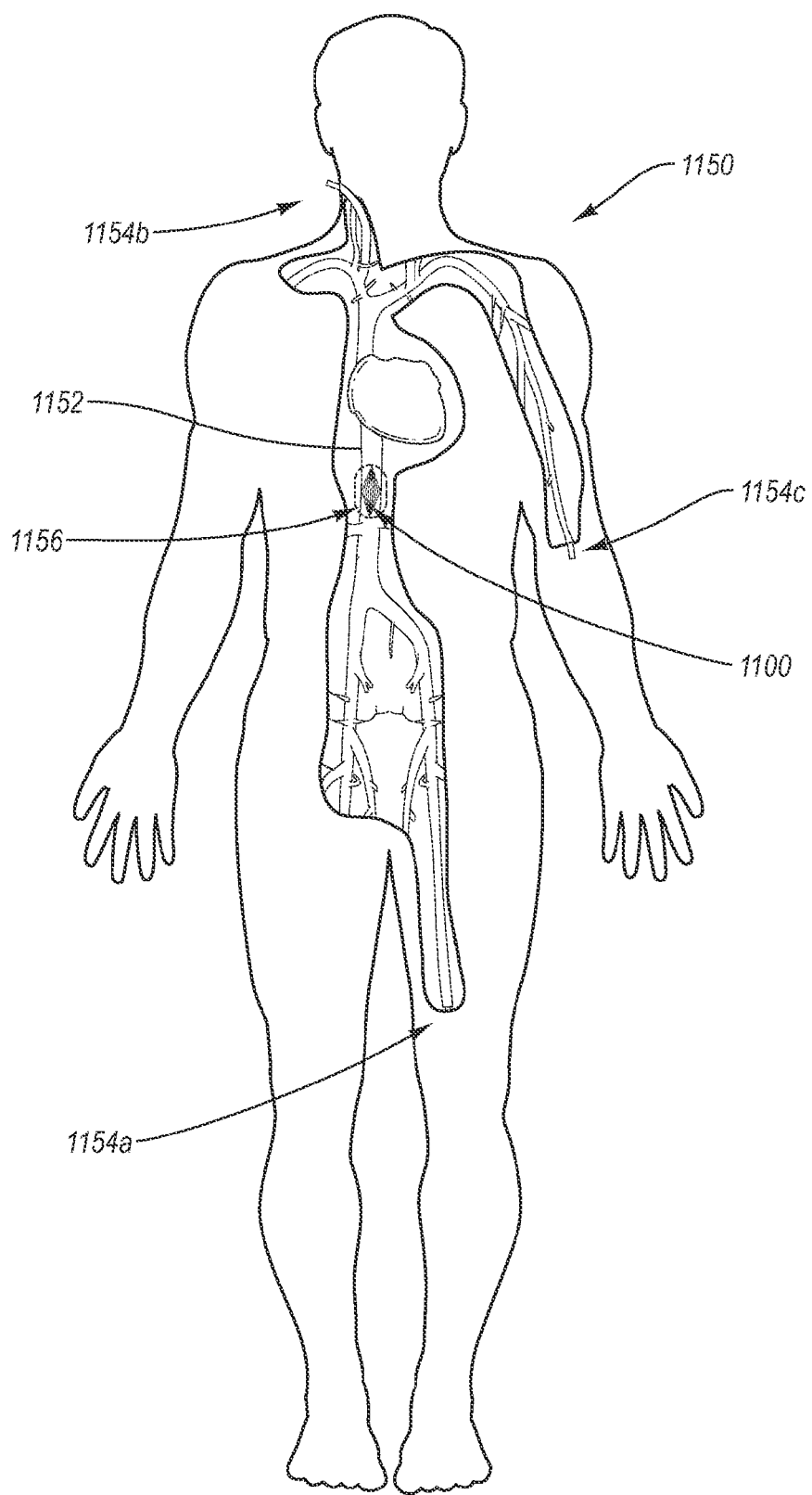
FIG. 11 illustrates an exemplary subject for an implantable lumen filter.

FIG. 11 illustrates an exemplary subject 1150 for an implantable lumen filter 1100. The implantable lumen filter 1100 may be functionally similar to the implantable lumen filters 100, 200, 300, 400, 500, 600, 700, 800, 900, 1000 previously described above and shown in FIGS. 1-10 in most respects, wherein certain features will not be described in relation to this configuration wherein those components may function in the manner as described above and are hereby incorporated into the configuration described below. Like structures and/or components are given like reference numerals. Additionally, the implantable lumen filter 1100 may incorporate at least one component of the implantable lumen filters 100, 200, 300, 400, 500, 600, 700, 800, 900, 1000, and 1200 described in connection with FIGS. 1-10 and 12, respectively.

Although many of the embodiments herein may describe an implantable lumen filter 1100, other filters may be deployed and/or retrieved using at least one embodiment of a filter retrieval system described herein. The filter 1100 may be implanted in a body lumen 1152 of the subject 1150. The filter 1100 may be inserted and/or retrieved through an access site 1154a, 1154b, 1154c. In the present embodiment, the access site may include a femoral artery access site 1154a, a jugular vein access site 1154b, a radial vein access site 1154c, femoral vein, brachial vein, brachial artery, other access sites, or combinations thereof. For instance, the filter 1100 may be inserted through the femoral artery access site 1154a and retrieved through the jugular or radial vein access site 1154b, 1154c. In another example, the filter 1100 may be inserted through the jugular vein access site 1154b and retrieved through the femoral artery or radial vein access site 1154a, 1154c. In a further example, the filter 1100 may be inserted through the radial vein access site 1154c and retrieved through the femoral artery or jugular vein access site 1154a, 1154b.

The filter 1100 may be inserted and retrieved through the radial vein access site 1154c. Additionally, the filter 1100 may be inserted and retrieved through the jugular vein access site 1154b. Further, the filter 1100 may be inserted and retrieved through the femoral artery access site 1154a.

The filter 1100 may be deployed near a deployment site 1156. In the present embodiment, the deployment site 1156 may include a location within the inferior vena cava. In other embodiments, other deployment sites may be used, such as the superior vena cava. For example, the deployment site 1156 may include all larger veins.

As mentioned above, some body lumen filters typically use jugular, antecubital, or other access sites for retrieval because they are typically not configured to be retrieved through the femoral access. Retrieval through the same access site through which the filter was deployed may be desired. At least one embodiment of a filter retrieval system may provide for retrieval through the same access site through which the filter was deployed.

FIGS. 12A-12G illustrate various steps in the deployment of an implantable lumen filter 1200. The implantable lumen filter 1200 may be functionally similar to the implantable lumen filters 100, 200, 300, 400, 500, 600, 700, 800, 900, 1000, 1100 previously described above and shown in FIGS. 1-11 in most respects, wherein certain features will not be described in relation to this configuration wherein those components may function in the manner as described above and are hereby incorporated into the configuration described below. Like structures and/or components are given like reference numerals. Additionally, the implantable lumen filter 1200 may incorporate at least one component of the implantable lumen filters 100, 200, 300, 400, 500, 600, 700, 800, 900, 1000, and 1100 described in connection with FIGS. 1-11, respectively.

Figure 12A:
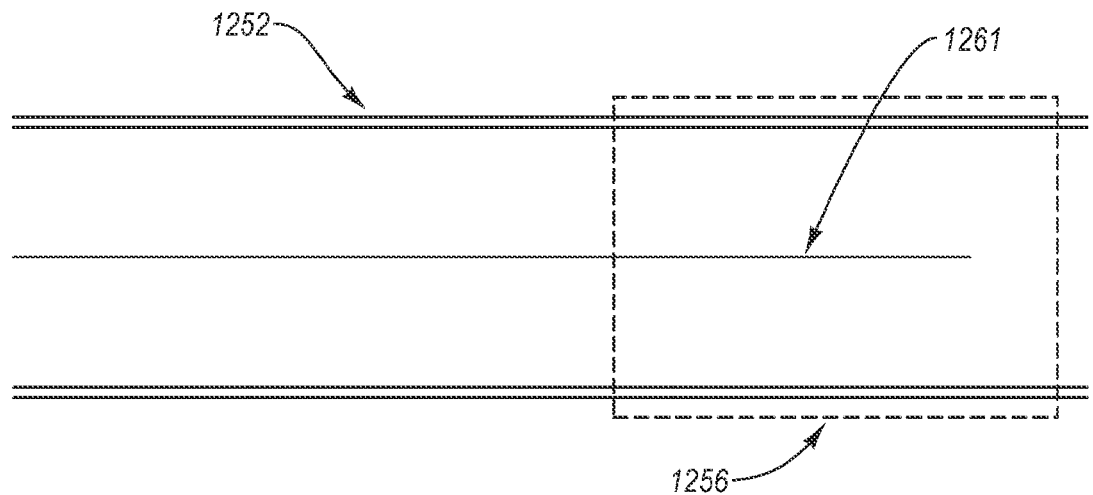
FIGS. 12A-12G' illustrate various steps in the deployment of an example implantable lumen filter.

FIG. 12A illustrates a deployment site 1256 within a body lumen 1252 with a guidewire 1261 partially inserted therethrough. The guidewire 1261 may be inserted through an access site (shown as 1154*a*, 1154*b*, 1154*c* in FIG. 11) toward the deployment site 1256. The guidewire 1261 may be used to locate the deployment site 1256. In other configurations, other methods may be used in addition to or instead of a guidewire 1261. For example, an imaging device, such as a fluoroscope, x-ray, and/or other imaging device may be used to locate the deployment site 1256.

Figure 12B:
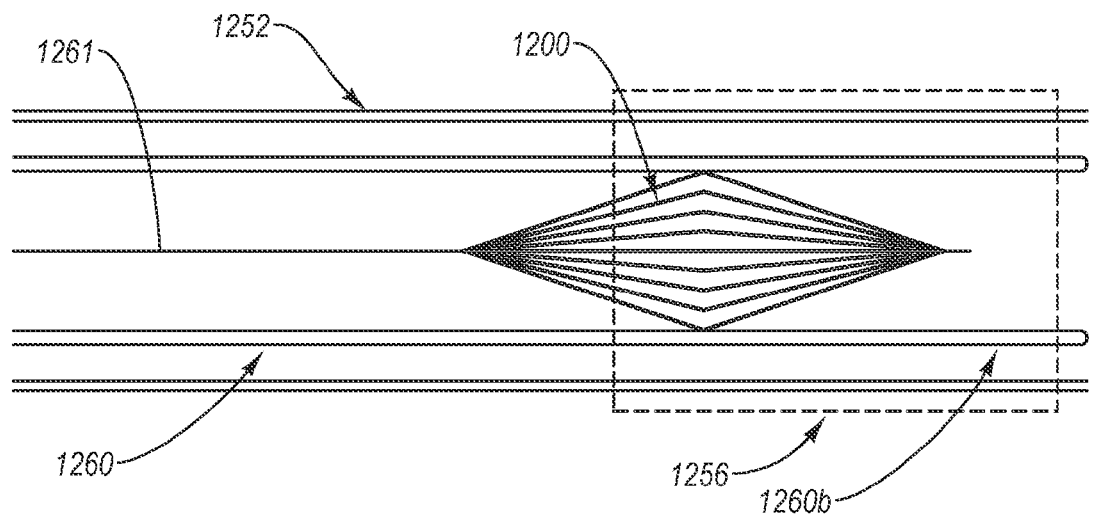

As shown in FIG. 12B, a delivery apparatus 1260 may use the guidewire 1261 to guide a distal end 1260*b* of the delivery apparatus 1260 toward the delivery site 1256. An implantable lumen filter 1200 may be disposed within the delivery apparatus 1260. The implantable lumen filter 1200, in the illustrated configuration, may be disposed within the delivery apparatus 1260 while in a collapsed state. While in the collapsed state, the implantable lumen filter 1200 may be longitudinally elongated with respect to a deployed state.

The guidewire 1261 may be removed after the distal end 1260*b* of the delivery apparatus 1260 is located near the delivery site 1256. Alternatively, the guidewire 1261 may remain.

Figure 12C:
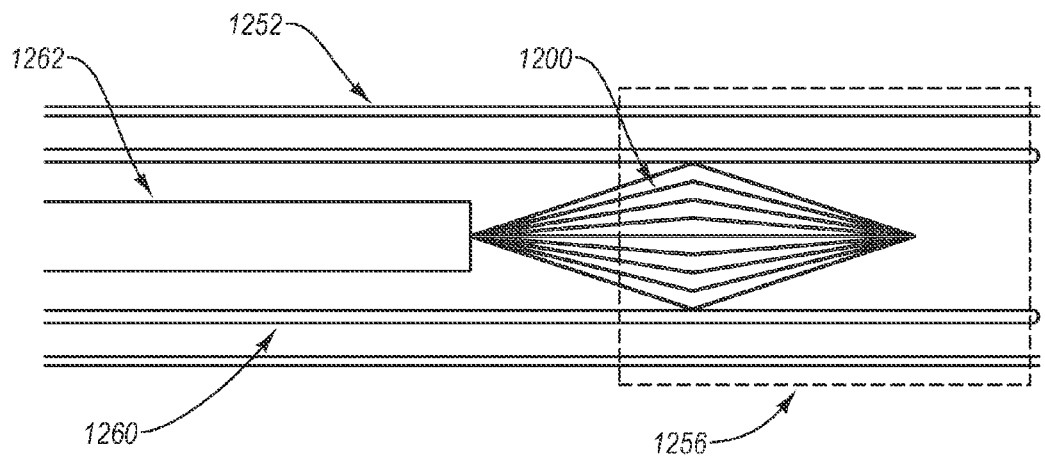

A deployment member 1262 may be inserted through the delivery apparatus 1260, as shown in FIG. 12C. The deployment member 1262 may be used to deploy the implantable lumen filter 1200. In the configuration shown in FIG. 12D, the deployment member 1262 may urge the implantable lumen filter 1200 toward the distal end 1260*b* of the delivery apparatus 1260 while the delivery apparatus 1260 may remain generally stationary.

The deployment member 1262 may urge the implantable lumen filter 1200 by abutting the proximal end 1202*a* of the filter 1200. The deployment member 1262 may include a receiving area (not shown), such as a convex portion configured and dimensioned to receive the proximal end 1202*a*, to facilitate urging the implantable lumen filter 1200 out of the delivery apparatus 1260.

Figure 12D:
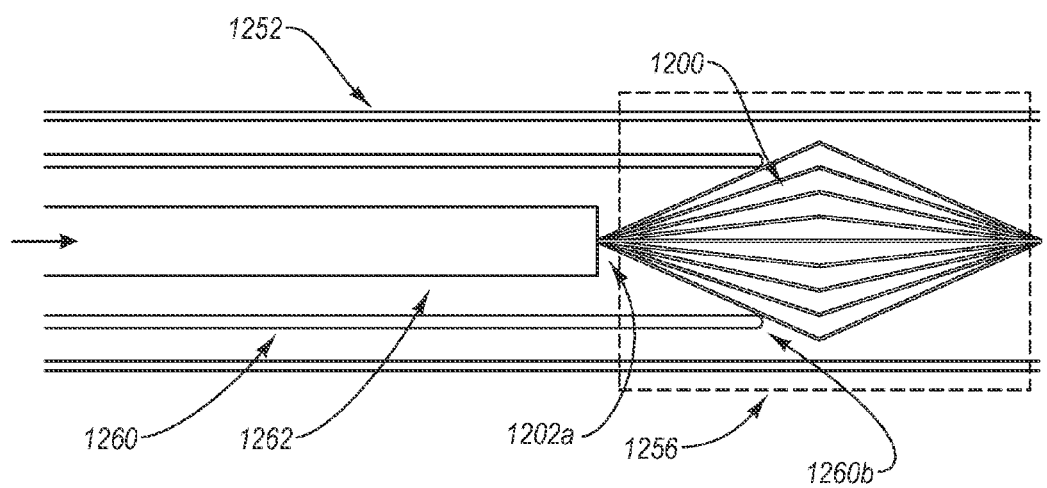
Figure 12D:
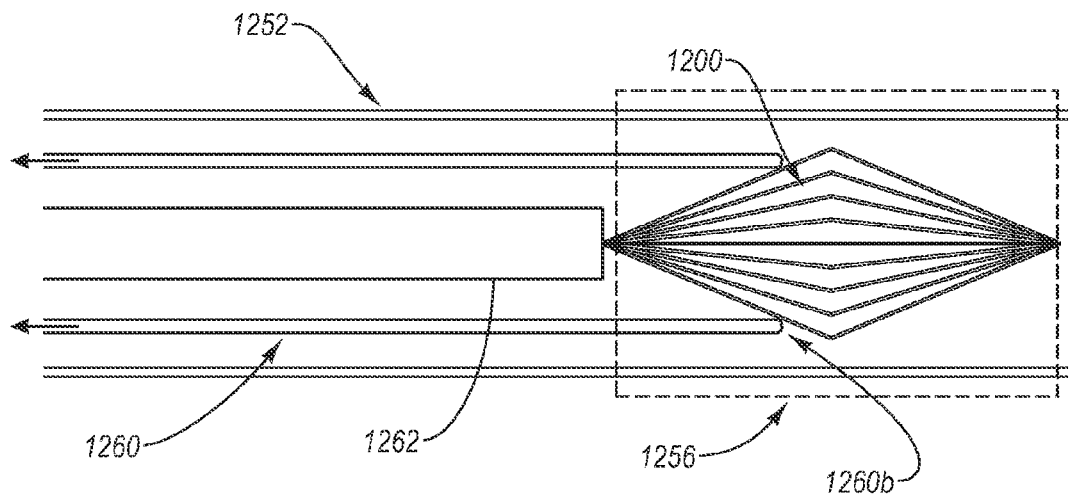

In the configuration shown in FIG. 12D', the delivery apparatus 1260 may be retracted while the deployment member 1262 may remain generally stationary. In other configurations, the delivery apparatus 1260 and/or the deployment member 1262 may cooperate to facilitate deployment of the implantable lumen filter 1200. For instance, the delivery apparatus 1260 may be retracted while the deployment member 1262 may urge the implantable lumen filter 1200 toward the distal end 1260*b* of the delivery apparatus 1260.

Figure 12E:
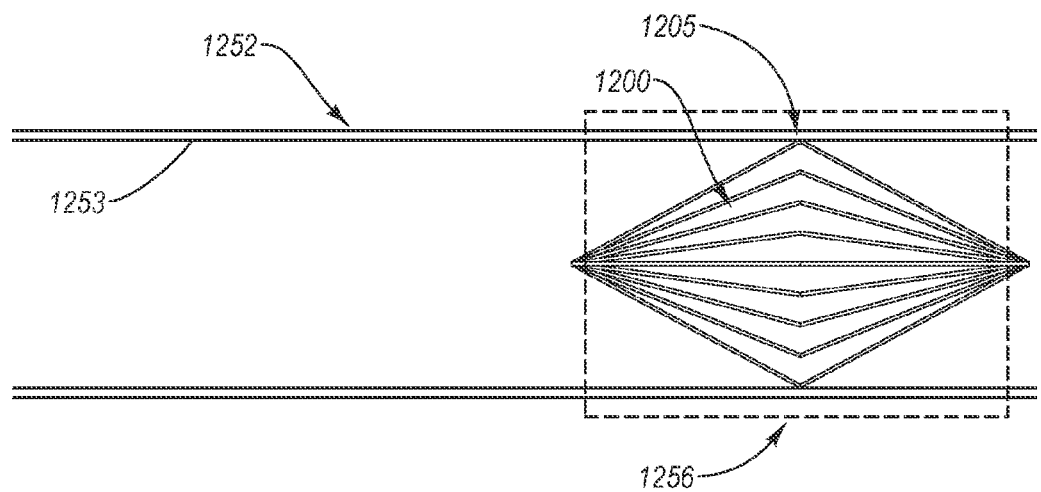

FIG. 12E illustrates a deployed implantable lumen filter 1200 within the body lumen 1252. In the deployed configuration, the implantable filter 1200 may engage an inside surface 1253 of the body lumen 1252. The apex 1205 of the implantable lumen filter may engage the inside surface 1253 of the body lumen 1252. In the deployed configuration, the implantable lumen filter 1200 may be longitudinally reduced with respect to a collapsed configuration.

Figure 12F:
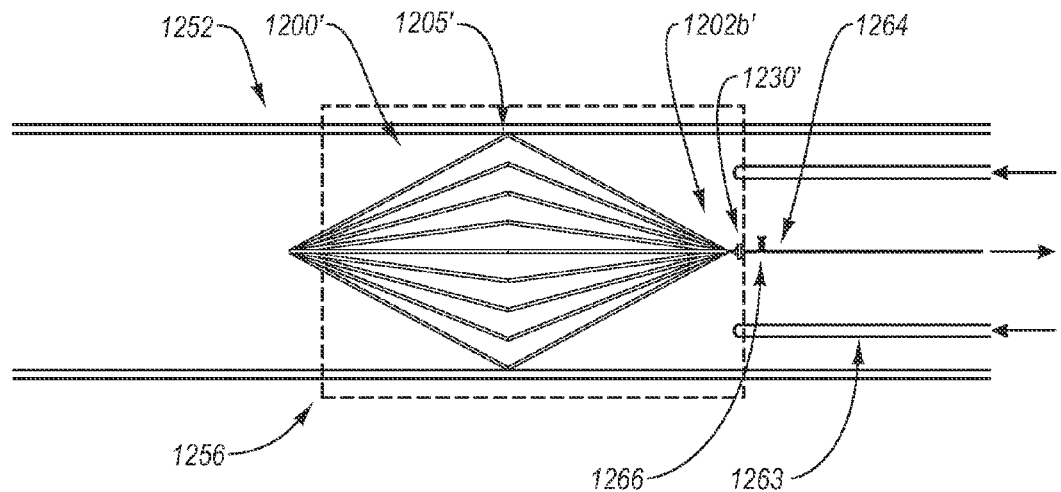
Figure 12F:
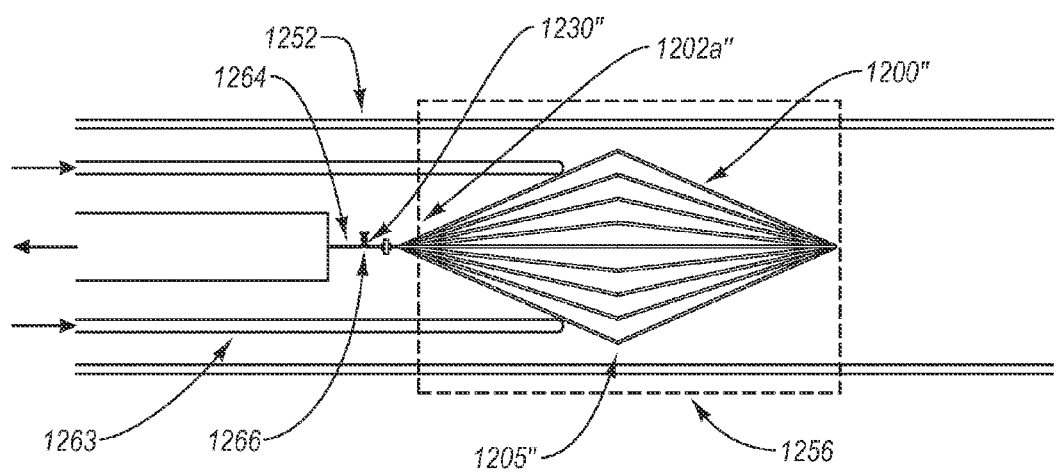
Figure 12G:
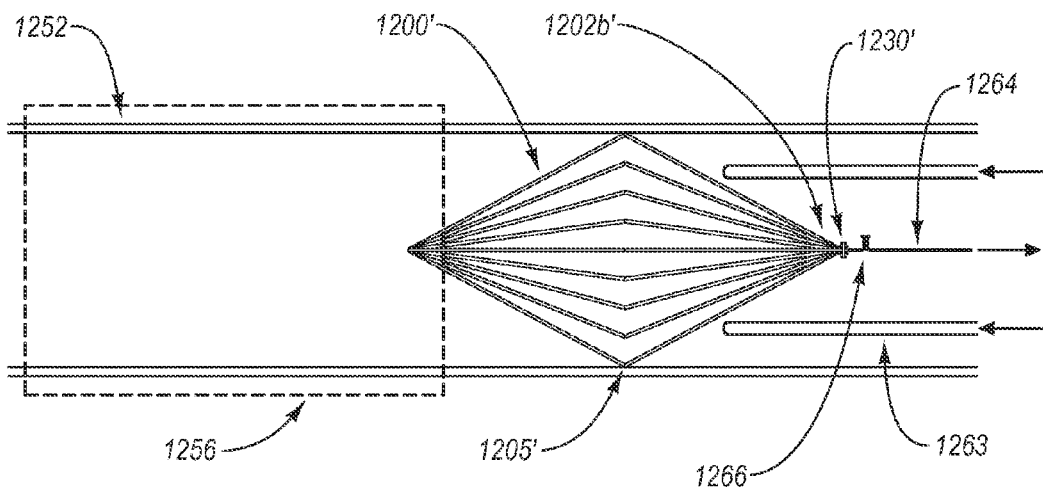
Figure 12G:
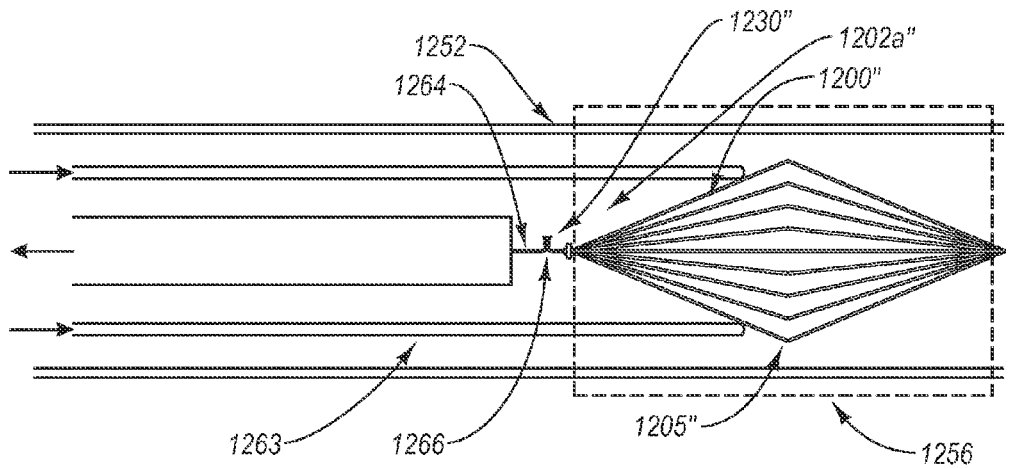

The implantable lumen filter 1200' shown in FIGS. 12F-12G may include a retrieval portion 1230' near the distal end 1202*b'* of the implantable lumen filter 1200'. The retrieval portion 1230' may be operatively connected to the distal end 1202*b'* of the implantable lumen filter 1200'.

The implantable lumen filter 1200' may be engaged by a retrieval member 1264. The retrieval member 1264 may include a retrieving mechanism 1266, such as a hook and/or other retaining mechanism, configured to engage the retrieval portion 1230'.

Upon engaging the retrieval portion 1230', the retrieval member 1264 may urge the implantable lumen filter 1200' into the retrieval apparatus 1263. For example, urging the implantable lumen filter 1200' toward the retrieval apparatus 1263 may facilitate disengaging the apex 1205'.

In the illustrated configuration, the retrieval apparatus 1263 and the retrieval member 1264 may both move in generally opposite directions to urge the implantable lumen filter 1200' into the retrieval apparatus 1263 into a compressed state, such that the implantable lumen filter 1200' may be longitudinally elongated with respect to a deployed state, as shown in FIG. 12G.

The implantable lumen filter 1200" shown in FIGS. 12F'-12G' is shown with a retrieval portion 1230" near the proximal end 1202*a"* of the implantable lumen filter 1200".

The implantable lumen filters 1200" may be engaged by a retrieval member 1264. The retrieval member 1264 may include a retrieving mechanism 1266, such as a hook and/or other retaining mechanism, configured to engage the retrieval portion 1230".

Upon engaging the retrieval portion 1230", the retrieval member 1264 may limit motion away from the retrieval member 1264. In the illustrated configuration, the retrieval member 1264 may remain generally stationary while the retrieval apparatus 1263 is advanced to urge the implantable lumen filter 1200" into the retrieval apparatus 1263. For example, advancing the retrieval apparatus 1263 may facilitate disengaging the apex 1205".

In the present configuration, the retrieval member 1264 remains generally stationary while the retrieval apparatus 1263 moves to urge the implantable lumen filter 1200" into the retrieval apparatus 1263 into a compressed state, such that the implantable lumen filter 1200" may be longitudinally elongated with respect to a deployed state, as shown in FIG. 12G'. In other configurations, both the retrieval apparatus 1263 and the retrieval member 1264 may move in generally opposite directions.

After the implantable devices 1200, 1200', 1200" are within the retrieval apparatus 1263, the retrieval apparatus 1263 and implantable devices 1200, 1200', 1200" may be withdrawn through an access site (shown as 1154*a*, 1154*b* in FIG. 11).

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

We claim:
1. An implantable lumen filter, comprising:
   a body comprising:
      a proximal portion having a generally-tapered outer surface, the outer surface of the proximal portion being defined by a plurality of elongated outer struts coupled together at a proximal end of the proximal portion and tapering outward towards a distal end of the proximal portion, adjacent outer struts of the proximal portion defining v-shaped apertures in the outer surface of the proximal portion;

a distal portion having a generally-tapered outer surface, the outer surface of the distal portion being defined by a plurality of elongated outer struts coupled together at a distal end of the distal portion and tapering outward away from each other towards a proximal end of the distal portion, the proximal end of the distal portion being coupled to the distal end of the proximal portion;

an apex joining the distal end of the proximal portion and the proximal end of the distal portion to form the body, and defining an outer dimension of the body, and a plurality of inner struts, the plurality of inner struts connect to the plurality of outer struts of the distal portion, extend across the apex, and connect with the plurality of outer struts of the proximal portion;

wherein at least one of the proximal and distal portions terminates at a hook configured for deploying or removing the body.

2. The implantable filter of claim 1, the body being transitionable from a collapsed state to a deployed state.

3. The implantable lumen filter of claim 1, the number and position of the outer struts of the proximal portion being selectively chosen to produce apertures of a selected size.

4. The implantable lumen filter of claim 1, further comprising a plurality of overhanging struts at least partially defining an annular region extending around the body proximate the apex.

5. The implantable lumen filter of claim 4, wherein the annular region is configured to collect, inhibit, or lyse particulates within a body lumen.

6. The implantable lumen filter of claim 1, at least a portion of the struts of the body including cobalt chromium and/or alloys thereof.

7. The implantable lumen filter of claim 1, at least a portion of the body being coated with a thrombo-resistant coating.

8. The implantable lumen filter of claim 1, in which the proximal portion and the distal portion are substantially symmetrical about a plane defined by the apex.

9. The implantable lumen filter of claim 8, wherein the proximal portion and the distal portion have opposing substantially conical shapes.

10. The implantable lumen filter of claim 1, the plurality of inner struts at least partially defining an inner dimension, the outer dimension and the inner dimension at least partially defining an annular region extending around the body proximate the apex.

11. The implantable lumen filter of claim 10, wherein the annular region is configured to collect, inhibit, or lyse particulates within a body lumen.

12. The implantable lumen filter of claim 1, the proximal portion being configured to direct particulates within a lumen radially outwards towards the outer dimension when the body is deployed within the lumen.

13. A method for filtering a body lumen, the method comprising:

longitudinally elongating an implantable lumen filter such that the implantable lumen filter has a reduced dimension, the implantable lumen filter including a body comprising:

a proximal portion having a generally-tapered outer surface, the outer surface of the proximal portion being defined by a plurality of elongated outer struts coupled together at a proximal end of the proximal portion and tapering outward towards a distal end of the proximal portion, adjacent outer struts of the proximal portion defining v-shaped apertures in the outer surface of the proximal portion;

a distal portion having a generally-tapered outer surface, the outer surface of the distal portion being defined by a plurality of elongated outer struts coupled together at a distal end of the distal portion and tapering outward towards a proximal end of the distal portion, the proximal end of the distal portion being coupled to the distal end of the proximal portion; and an apex extending around the body proximate the distal end of the proximal portion and defining an outer dimension of the body;

a plurality of inner struts, the plurality of inner struts connect to the plurality of outer struts of the distal portion, extend across the apex, and connect with the plurality of outer struts of the proximal portion;

wherein at least one of the proximal and distal portions terminates at a hook configured for deploying or removing the body;

delivering the implantable lumen filter to a desired deployment site within the body lumen; and longitudinally reducing the implantable lumen filter such that the implantable lumen filter has an enlarged outer dimension and applies radial force to an inner wall of the body lumen.

14. An implantable lumen filter, comprising:

a body comprising:

a proximal portion having a generally-tapered outer surface, the outer surface of the proximal portion being defined by a plurality of elongated outer struts coupled together at a proximal end of the proximal portion and tapering outward towards a distal end of the proximal portion, adjacent outer struts of the proximal portion defining v-shaped apertures in the outer surface of the proximal portion, the proximal portion terminating in a hook configured for deploying or removing the body, the distal end of at least one outer strut of the proximal portion being angled in a direction transverse to a longitudinal axis of the body and a remainder of the outer strut;

a distal portion having a generally-tapered outer surface, the outer surface of the distal portion being defined by a plurality of elongated outer struts coupled together at a distal end of the distal portion and tapering outward towards a proximal end of the distal portion, the proximal end of the distal portion being coupled to the distal end of the proximal portion, the distal portion terminating in a hook configured for deploying or removing the body;

an apex extending around the body and defining an outer dimension of the body; and a plurality of inner struts, the plurality of inner struts connect to the plurality of outer struts of the distal portion, extend across the apex, and connect with the plurality of outer struts of the proximal portion;

an annular region extending around the body proximate the apex, the annular region being configured to collect, inhibit, and/or lyse particulates within a lumen, the annular region being at least partially defined by the outer dimension, the proximal portion being configured to direct particulates within a lumen radially outwardly towards the annular region when the body is deployed within the lumen with the proximal portion being deployed on the upstream side of the body.

* * * * *